United States Patent
Norchi et al.

(10) Patent No.: US 12,390,552 B2
(45) Date of Patent: Aug. 19, 2025

(54) SELF-ASSEMBLING PEPTIDE GEL FORMULATION AND METHODS OF USE

(71) Applicant: Arch Biosurgery, Inc., Framingham, MA (US)

(72) Inventors: Terrence Norchi, Natick, MA (US); Chirag Shah, North Attleboro, MA (US); Rutledge Ellis-Behnke, Myrtle Beach, SC (US)

(73) Assignee: Arch Biosurgery, Inc., Framingham, MA (US)

( * ) Notice: Subject to any disclaimer, the term of this patent is extended or adjusted under 35 U.S.C. 154(b) by 0 days.

(21) Appl. No.: 17/148,180

(22) Filed: Jan. 13, 2021

(65) Prior Publication Data

US 2021/0213161 A1 Jul. 15, 2021

Related U.S. Application Data

(60) Provisional application No. 63/063,704, filed on Aug. 10, 2020, provisional application No. 62/960,550, filed on Jan. 13, 2020.

(51) Int. Cl.
| | |
|---|---|
| *A61L 27/22* | (2006.01) |
| *A61L 27/52* | (2006.01) |
| *A61L 27/58* | (2006.01) |
| *C07K 7/08* | (2006.01) |

(52) U.S. Cl.
CPC ............... *A61L 27/22* (2013.01); *A61L 27/52* (2013.01); *A61L 27/58* (2013.01); *C07K 7/08* (2013.01); *A61L 2400/04* (2013.01); *A61L 2400/06* (2013.01); *C07K 2319/735* (2013.01)

(58) Field of Classification Search
None
See application file for complete search history.

(56) References Cited

U.S. PATENT DOCUMENTS

2015/0105336 A1* 4/2015 Takamura ................ C07K 7/08
514/21.4
2020/0009214 A1* 1/2020 Gil .......................... A61K 47/42

OTHER PUBLICATIONS

Anonymous "PuraMatrix Synthetic Peptide Hydrogels" https://product.statnano.com/product/8559/puramatrix%C2%AE-synthetic-peptide-hydrogels (Year: 2017).*

* cited by examiner

*Primary Examiner* — Melissa L Fisher
*Assistant Examiner* — Zachary J Miknis
(74) *Attorney, Agent, or Firm* — Kilpatrick Townsend & Stockton LLP

(57) ABSTRACT

Compositions containing self-assembling peptides and/or self-assembling peptidomimetics ("self-assembling peptides") can be used to create a long-lasting "lift" or means of elevating tissue to be resected, dissected, manipulated or repaired, as a bulking agent, or as a tissue forming matrix by injection of a solution that forms a solid gel in situ, which is stable for a prolonged period of time from days to a month, is hemostatic, and may prevent adhesions. These self-assembling peptides and methods of use thereof enable better separation of tissues and visualization of margins, more durable and robust lifts, less need for frequent injections that carry risk of undesired perforation, and simultaneous management of adverse effects, such as bleeding, leaking, inflammation and iatrogenic injury during endoscopic, laparoscopic or other minimally invasive, or open surgical procedures in and/or on the body.

24 Claims, No Drawings
Specification includes a Sequence Listing.

SEQUENCE LISTING

```
<160> NUMBER OF SEQ ID NOS: 104

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 2

Ser Gly Ser Gly Ser Gly Ser Gly Ser Gly Ser Gly Ser Gly Ser Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 3

Ser Ala Ser Ala Ser Ala Ser Ala Ser Ala Ser Ala Ser Ala Ser Ala
```

```
                1               5                  10                 15

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 4

Ser Val Ser Val Ser Val Ser Val Ser Val Ser Val Ser Val Ser Val
1               5                  10                 15

<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 5

Ser Leu Ser Leu Ser Leu Ser Leu Ser Leu Ser Leu Ser Leu Ser Leu
1               5                  10                 15

<210> SEQ ID NO 6
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 6

Ser Ile Ser Ile Ser Ile Ser Ile Ser Ile Ser Ile Ser Ile Ser Ile
1               5                  10                 15

<210> SEQ ID NO 7
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 7

Ser Met Ser Met Ser Met Ser Met Ser Met Ser Met Ser Met Ser Met
1               5                  10                 15

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 8

Ser Phe Ser Phe Ser Phe Ser Phe Ser Phe Ser Phe Ser Phe Ser Phe
1               5                  10                 15

<210> SEQ ID NO 9
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 9

Ser Trp Ser Trp Ser Trp Ser Trp Ser Trp Ser Trp Ser Trp Ser Trp
1               5                  10                 15
```

```
<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

Ser Pro Ser Pro Ser Pro Ser Pro Ser Pro Ser Pro Ser Pro Ser Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 11

Thr Gly Thr Gly Thr Gly Thr Gly Thr Gly Thr Gly Thr Gly Thr Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

Thr Ala Thr Ala Thr Ala Thr Ala Thr Ala Thr Ala Thr Ala Thr Ala
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 13

Thr Val Thr Val Thr Val Thr Val Thr Val Thr Val Thr Val Thr Val
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 14

Thr Leu Thr Leu Thr Leu Thr Leu Thr Leu Thr Leu Thr Leu Thr Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 15

Thr Ile Thr Ile Thr Ile Thr Ile Thr Ile Thr Ile Thr Ile Thr Ile
1               5                   10                  15
```

```
<210> SEQ ID NO 16
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 16

Thr Met Thr Met Thr Met Thr Met Thr Met Thr Met Thr Met Thr Met
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 17

Thr Phe Thr Phe Thr Phe Thr Phe Thr Phe Thr Phe Thr Phe Thr Phe
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 18

Thr Trp Thr Trp Thr Trp Thr Trp Thr Trp Thr Trp Thr Trp Thr Trp
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 19

Thr Pro Thr Pro Thr Pro Thr Pro Thr Pro Thr Pro Thr Pro Thr Pro
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 20

Cys Gly Cys Gly Cys Gly Cys Gly Cys Gly Cys Gly Cys Gly Cys Gly
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 21

Cys Ala Cys Ala Cys Ala Cys Ala Cys Ala Cys Ala Cys Ala Cys Ala
1               5                   10                  15
```

```
<210> SEQ ID NO 22
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 22

Cys Val Cys Val Cys Val Cys Val Cys Val Cys Val Cys Val Cys Val
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 23

Cys Leu Cys Leu Cys Leu Cys Leu Cys Leu Cys Leu Cys Leu Cys Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 24

Cys Ile Cys Ile Cys Ile Cys Ile Cys Ile Cys Ile Cys Ile Cys Ile
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 25

Cys Met Cys Met Cys Met Cys Met Cys Met Cys Met Cys Met Cys Met
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 26

Cys Phe Cys Phe Cys Phe Cys Phe Cys Phe Cys Phe Cys Phe Cys Phe
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 27

Cys Trp Cys Trp Cys Trp Cys Trp Cys Trp Cys Trp Cys Trp Cys
1               5                   10                  15

<210> SEQ ID NO 28
```

<211> LENGTH: 16
<212> TYPE: PRT
<213> ORGANISM: Artificial Sequence
<220> FEATURE:
<223> OTHER INFORMATION: Synthetic Peptide

<400> SEQUENCE: 28

Cys Pro Cys Pro Cys Pro Cys Pro Cys Pro Cys Pro Cys Pro Cys Pro
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 29

Tyr Gly Tyr Gly Tyr Gly Tyr Gly Tyr Gly Tyr Gly Tyr Gly Tyr Gly
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 30

Tyr Ala Tyr Ala Tyr Ala Tyr Ala Tyr Ala Tyr Ala Tyr Ala Tyr Ala
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 31

Tyr Val Tyr Val Tyr Val Tyr Val Tyr Val Tyr Val Tyr Val Tyr Val
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 32

Tyr Leu Tyr Leu Tyr Leu Tyr Leu Tyr Leu Tyr Leu Tyr Leu Tyr Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 33

Tyr Ile Tyr Ile Tyr Ile Tyr Ile Tyr Ile Tyr Ile Tyr Ile Tyr Ile
1               5                   10                  15

<210> SEQ ID NO 34
<211> LENGTH: 16

```
<212> TYPE: PRT
<213> ORGANISM: Artificial Sequence
<220> FEATURE:
<223> OTHER INFORMATION: Synthetic Peptide

<400> SEQUENCE: 34

Tyr Met Tyr Met Tyr Met Tyr Met Tyr Met Tyr Met Tyr Met Tyr Met
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 35

Tyr Phe Tyr Phe Tyr Phe Tyr Phe Tyr Phe Tyr Phe Tyr Phe Tyr Phe
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 36

Tyr Trp Tyr Trp Tyr Trp Tyr Trp Tyr Trp Tyr Trp Tyr Trp Tyr Trp
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 37

Tyr Pro Tyr Pro Tyr Pro Tyr Pro Tyr Pro Tyr Pro Tyr Pro Tyr Pro
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 38

Asn Gly Asn Gly Asn Gly Asn Gly Asn Gly Asn Gly Asn Gly Asn Gly
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 39

Asn Ala Asn Ala Asn Ala Asn Ala Asn Ala Asn Ala Asn Ala Asn Ala
1               5                   10                  15

<210> SEQ ID NO 40
<211> LENGTH: 16
<212> TYPE: PRT
```

```
<213> ORGANISM: Artificial Sequence
<220> FEATURE:
<223> OTHER INFORMATION: Synthetic Peptide

<400> SEQUENCE: 40

Asn Val Asn Val Asn Val Asn Val Asn Val Asn Val Asn Val Asn Val
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 41

Asn Leu Asn Leu Asn Leu Asn Leu Asn Leu Asn Leu Asn Leu Asn Leu
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 42

Asn Ile Asn Ile Asn Ile Asn Ile Asn Ile Asn Ile Asn Ile Asn Ile
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 43

Asn Met Asn Met Asn Met Asn Met Asn Met Asn Met Asn Met Asn Met
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 44

Asn Phe Asn Phe Asn Phe Asn Phe Asn Phe Asn Phe Asn Phe Asn Phe
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 45

Asn Trp Asn Trp Asn Trp Asn Trp Asn Trp Asn Trp Asn Trp Asn Trp
1               5                   10                  15

<210> SEQ ID NO 46
<211> LENGTH: 16
<212> TYPE: PRT
<213> ORGANISM: Artificial Sequence
```

```
<220> FEATURE:
<223> OTHER INFORMATION: Synthetic Peptide

<400> SEQUENCE: 46

Asn Pro Asn Pro Asn Pro Asn Pro Asn Pro Asn Pro Asn Pro Asn Pro
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 47

Gln Gly Gln Gly Gln Gly Gln Gly Gln Gly Gln Gly Gln Gly Gln Gly
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 48

Gln Ala Gln Ala Gln Ala Gln Ala Gln Ala Gln Ala Gln Ala Gln Ala
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 49

Gln Val Gln Val Gln Val Gln Val Gln Val Gln Val Gln Val Gln Val
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 50

Gln Leu Gln Leu Gln Leu Gln Leu Gln Leu Gln Leu Gln Leu Gln Leu
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 51

Gln Ile Gln Ile Gln Ile Gln Ile Gln Ile Gln Ile Gln Ile Gln Ile
1               5                   10                  15

<210> SEQ ID NO 52
<211> LENGTH: 16
<212> TYPE: PRT
<213> ORGANISM: Artificial Sequence
<220> FEATURE:
```

<223> OTHER INFORMATION: Synthetic Peptide

<400> SEQUENCE: 52

Gln Met Gln Met Gln Met Gln Met Gln Met Gln Met Gln Met Gln Met
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 53

Gln Phe Gln Phe Gln Phe Gln Phe Gln Phe Gln Phe Gln Phe Gln Phe
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 54

Gln Trp Gln Trp Gln Trp Gln Trp Gln Trp Gln Trp Gln Trp Gln Trp
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 55

Gln Pro Gln Pro Gln Pro Gln Pro Gln Pro Gln Pro Gln Pro Gln Pro
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 56

Ala Glu Ala Lys Ala Glu Ala Lys Ala Glu Ala Lys Ala Glu Ala Lys
1               5                   10                  15

<210> SEQ ID NO 57
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 57

Arg Ala Asp Ala
1

<210> SEQ ID NO 58
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 58

Arg Ala Glu Ala Arg Ala Glu Ala Arg Ala Glu Ala Arg Ala Glu Ala
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 59

Lys Ala Asp Ala Lys Ala Asp Ala Lys Ala Asp Ala Lys Ala Asp Ala
1               5                   10                  15

<210> SEQ ID NO 60
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 60

Ala Arg Ala Asp Ala Arg Ala Asp Ala Arg Ala Asp Ala
1               5                   10

<210> SEQ ID NO 61
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 61

Arg Ala Asp Ala Arg Ala Asp Ala Arg Ala Asp Ala Arg Ala Asp Ala
1               5                   10                  15

Arg Ala Asp Ala
            20

<210> SEQ ID NO 62
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 62

Ala Arg Ala Asp Ala Arg Ala Asp Ala Arg Ala Asp Ala Arg Ala Asp
1               5                   10                  15

Ala Arg Ala Asp Ala
            20

<210> SEQ ID NO 63
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 63

Ala Arg Ala Asp Ala Arg Ala Asp Ala Arg Ala Asp Ala Arg Ala Asp
1               5                   10                  15

Ala

<210> SEQ ID NO 64
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 64

Arg Leu Asp Leu Arg Leu Asp Leu Arg Leu Asp Leu Arg Leu Asp Leu
1               5                   10                  15

<210> SEQ ID NO 65
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 65

Arg Leu Asp Leu
1

<210> SEQ ID NO 66
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 66

Arg Leu Asp Leu Arg Leu
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 67

Arg Ala Asp Ala Arg Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 68

Leu Arg Leu Asp Leu Arg
1               5

<210> SEQ ID NO 69
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 69

Ile Glu Ile Lys Ile Glu Ile Lys Ile Glu Ile Lys Ile
1               5                   10

```
<210> SEQ ID NO 70
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 70

Ile Glu Ile Lys Ile Glu Ile Lys Ile Glu Ile Lys Ile Glu Ile Lys
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 71

Ile Glu Ile Lys Ile Glu Ile Lys Ile Glu Ile Lys Ile Glu Ile Lys
1               5                   10                  15

Ile

<210> SEQ ID NO 72
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 72

Ile Glu Ile Lys Ile Glu Ile Lys Ile Glu Ile Lys Ile Glu Ile Lys
1               5                   10                  15

Ile Glu Ile Lys
            20

<210> SEQ ID NO 73
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 73

Ile Glu Ile Lys Ile Glu Ile Lys Ile Glu Ile Lys Ile Glu Ile Lys
1               5                   10                  15

Ile Glu Ile Lys Ile
            20

<210> SEQ ID NO 74
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 74

Ile Glu Ile Lys Ile Glu Ile Lys Ile Glu Ile Lys
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Synthetic Peptide
```

```
<400> SEQUENCE: 75

Glu Ile Lys Ile Glu Ile Lys Ile Glu Ile Lys Ile Glu Ile Lys Ile
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 76

Glu Ala Lys Ala Glu Ala Lys Ala Glu Ala Lys Ala Glu Ala Lys Ala
1               5                   10                  15

<210> SEQ ID NO 77
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 77

Glu Ala Lys Ala
1

<210> SEQ ID NO 78
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 78

Glu Ala Lys Ala Glu Ala Lys Ala Glu Ala
1               5                   10

<210> SEQ ID NO 79
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 79

Glu Ala Lys Ala Glu Ala Lys Ala Glu Ala Lys Ala Glu Ala Lys Ala
1               5                   10                  15

Glu Ala Lys Ala
            20

<210> SEQ ID NO 80
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 80

Ala Glu Ala Lys Ala Glu Ala Lys Ala Glu Ala Lys Ala Glu Ala Lys
1               5                   10                  15

Ala

<210> SEQ ID NO 81
<211> LENGTH: 13
```

```
<212> TYPE: PRT
<213> ORGANISM: Artificial Sequence
<220> FEATURE:
<223> OTHER INFORMATION: Synthetic Peptide

<400> SEQUENCE: 81

Ala Glu Ala Lys Ala Glu Ala Lys Ala Glu Ala Lys Ala
1               5                   10

<210> SEQ ID NO 82
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 82

Arg Ala Asp Ala Arg Ala Asp Ala Arg Ala Asp Ala Arg Ala Asp Ala
1               5                   10                  15

Arg Ala

<210> SEQ ID NO 83
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: D-alanine
<220> FEATURE:
<221> NAME/KEY: MISC_FEATURE
<222> LOCATION: (3)..(3)
<223> OTHER INFORMATION: D-aspartic acid
<220> FEATURE:
<221> NAME/KEY: MISC_FEATURE
<222> LOCATION: (4)..(4)
<223> OTHER INFORMATION: D-alanine
<220> FEATURE:
<221> NAME/KEY: MISC_FEATURE
<222> LOCATION: (5)..(5)
<223> OTHER INFORMATION: D-arginine
<220> FEATURE:
<221> NAME/KEY: MISC_FEATURE
<222> LOCATION: (6)..(6)
<223> OTHER INFORMATION: D-alanine
<220> FEATURE:
<221> NAME/KEY: MISC_FEATURE
<222> LOCATION: (7)..(7)
<223> OTHER INFORMATION: D-aspartic acid
<220> FEATURE:
<221> NAME/KEY: MISC_FEATURE
<222> LOCATION: (8)..(8)
<223> OTHER INFORMATION: D-alanine
<220> FEATURE:
<221> NAME/KEY: MISC_FEATURE
<222> LOCATION: (9)..(9)
<223> OTHER INFORMATION: D-arginine
<220> FEATURE:
<221> NAME/KEY: MISC_FEATURE
<222> LOCATION: (10)..(10)
<223> OTHER INFORMATION: D-alanine
<220> FEATURE:
<221> NAME/KEY: MISC_FEATURE
<222> LOCATION: (11)..(11)
<223> OTHER INFORMATION: D-aspartic acid
<220> FEATURE:
<221> NAME/KEY: MISC_FEATURE
<222> LOCATION: (12)..(12)
```

```
<223> OTHER INFORMATION: D-alanine
<220> FEATURE:
<221> NAME/KEY: MISC_FEATURE
<222> LOCATION: (13)..(12)
<223> OTHER INFORMATION: D-arginine
<220> FEATURE:
<221> NAME/KEY: MISC_FEATURE
<222> LOCATION: (14)..(14)
<223> OTHER INFORMATION: D-alanine
<220> FEATURE:
<221> NAME/KEY: MISC_FEATURE
<222> LOCATION: (15)..(15)
<223> OTHER INFORMATION: D-aspartic acid
<220> FEATURE:
<221> NAME/KEY: MISC_FEATURE
<222> LOCATION: (16)..(16)
<223> OTHER INFORMATION: D-alanine

<400> SEQUENCE: 83

Arg Ala Asp Ala Arg Ala Asp Ala Arg Ala Asp Ala Arg Ala Asp Ala
1               5                   10                  15

<210> SEQ ID NO 84
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: D-alanine
<220> FEATURE:
<221> NAME/KEY: MISC_FEATURE
<222> LOCATION: (3)..(3)
<223> OTHER INFORMATION: D-aspartic acid
<220> FEATURE:
<221> NAME/KEY: MISC_FEATURE
<222> LOCATION: (4)..(4)
<223> OTHER INFORMATION: D-alanine
<220> FEATURE:
<221> NAME/KEY: MISC_FEATURE
<222> LOCATION: (5)..(5)
<223> OTHER INFORMATION: D-arginine
<220> FEATURE:
<221> NAME/KEY: MISC_FEATURE
<222> LOCATION: (6)..(6)
<223> OTHER INFORMATION: D-alanine
<220> FEATURE:
<221> NAME/KEY: MISC_FEATURE
<222> LOCATION: (7)..(7)
<223> OTHER INFORMATION: D-aspartic acid
<220> FEATURE:
<221> NAME/KEY: MISC_FEATURE
<222> LOCATION: (8)..(8)
<223> OTHER INFORMATION: D-alanine
<220> FEATURE:
<221> NAME/KEY: MISC_FEATURE
<222> LOCATION: (9)..(9)
<223> OTHER INFORMATION: D-arginine
<220> FEATURE:
<221> NAME/KEY: MISC_FEATURE
<222> LOCATION: (10)..(10)
<223> OTHER INFORMATION: D-alanine
<220> FEATURE:
<221> NAME/KEY: MISC_FEATURE
<222> LOCATION: (11)..(11)
<223> OTHER INFORMATION: D-aspartic acid
<220> FEATURE:
<221> NAME/KEY: MISC_FEATURE
<222> LOCATION: (12)..(12)
<223> OTHER INFORMATION: D-alanine
```

```
<400> SEQUENCE: 84

Arg Ala Asp Ala Arg Ala Asp Ala Arg Ala Asp Ala
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-glutamic acid
<220> FEATURE:
<221> NAME/KEY: MISC_FEATURE
<222> LOCATION: (2)..(2)
<223> OTHER INFORMATION: D-alanine
<220> FEATURE:
<221> NAME/KEY: MISC_FEATURE
<222> LOCATION: (3)..(3)
<223> OTHER INFORMATION: D-lysine
<220> FEATURE:
<221> NAME/KEY: MISC_FEATURE
<222> LOCATION: (4)..(4)
<223> OTHER INFORMATION: D-alanine
<220> FEATURE:
<221> NAME/KEY: MISC_FEATURE
<222> LOCATION: (5)..(5)
<223> OTHER INFORMATION: D-glutamic acid
<220> FEATURE:
<221> NAME/KEY: MISC_FEATURE
<222> LOCATION: (6)..(6)
<223> OTHER INFORMATION: D-alanine
<220> FEATURE:
<221> NAME/KEY: MISC_FEATURE
<222> LOCATION: (7)..(7)
<223> OTHER INFORMATION: D-lysine
<220> FEATURE:
<221> NAME/KEY: MISC_FEATURE
<222> LOCATION: (8)..(8)
<223> OTHER INFORMATION: D-alanine
<220> FEATURE:
<221> NAME/KEY: MISC_FEATURE
<222> LOCATION: (9)..(9)
<223> OTHER INFORMATION: D-glutamic acid
<220> FEATURE:
<221> NAME/KEY: MISC_FEATURE
<222> LOCATION: (10)..(10)
<223> OTHER INFORMATION: D-alanine
<220> FEATURE:
<221> NAME/KEY: MISC_FEATURE
<222> LOCATION: (11)..(11)
<223> OTHER INFORMATION: D-lysine
<220> FEATURE:
<221> NAME/KEY: MISC_FEATURE
<222> LOCATION: (12)..(12)
<223> OTHER INFORMATION: D-alanine

<400> SEQUENCE: 85

Glu Ala Lys Ala Glu Ala Lys Ala Glu Ala Lys Ala
1               5                   10

<210> SEQ ID NO 86
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-glutamic acid
<220> FEATURE:
<221> NAME/KEY: MISC_FEATURE
```

```
<222> LOCATION: (2)..(2)
<223> OTHER INFORMATION: D-alanine
<220> FEATURE:
<221> NAME/KEY: MISC_FEATURE
<222> LOCATION: (3)..(3)
<223> OTHER INFORMATION: D-lysine
<220> FEATURE:
<221> NAME/KEY: MISC_FEATURE
<222> LOCATION: (4)..(4)
<223> OTHER INFORMATION: D-alanine

<400> SEQUENCE: 86

Glu Ala Lys Ala
1

<210> SEQ ID NO 87
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-arginine
<220> FEATURE:
<221> NAME/KEY: MISC_FEATURE
<222> LOCATION: (2)..(2)
<223> OTHER INFORMATION: D-alanine
<220> FEATURE:
<221> NAME/KEY: MISC_FEATURE
<222> LOCATION: (3)..(3)
<223> OTHER INFORMATION: D-aspartic acid
<220> FEATURE:
<221> NAME/KEY: MISC_FEATURE
<222> LOCATION: (4)..(4)
<223> OTHER INFORMATION: D-alanine

<400> SEQUENCE: 87

Arg Ala Asp Ala
1

<210> SEQ ID NO 88
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 88

Arg Ala Asp Ala Arg Ala Asp Ala
1               5

<210> SEQ ID NO 89
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 89

Glu Ala Arg Ala Glu Ala Arg Ala Glu Ala Arg Ala Glu Ala Arg Ala
1               5                   10                  15

<210> SEQ ID NO 90
<211> LENGTH: 12
<212> TYPE: PRT
<213> ORGANISM: Artificial Sequence
<220> FEATURE:
<223> OTHER INFORMATION: Synthetic Peptide
```

```
<400> SEQUENCE: 90

Glu Ala Arg Ala Glu Ala Arg Ala Glu Ala Arg Ala
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 91

Glu Ala Arg Ala Glu Ala Arg Ala Glu
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 92

Glu Ala Arg Ala
1

<210> SEQ ID NO 93
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 93

Arg Ala Arg Ala Arg Ala Asp Ala Asp Ala Asp Ala
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 94

Arg Ala Arg Ala Arg Ala Arg Ala Asp Ala Asp Ala Asp Ala Asp Ala
1               5                   10                  15

<210> SEQ ID NO 95
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 95

Arg Arg Arg Arg Asp Asp Asp Asp
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 96
```

```
Gly Gly Gly Gly Ser Ser Ser Ser
1               5

<210> SEQ ID NO 97
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 97

Gly Gln Gly Gln
1

<210> SEQ ID NO 98
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 98

Gly Gly Gln Gln Gly Gly
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 99

Gly Gln Gln Gly Gln Gln Gly
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 100

Gly Gly Gln Gly Gly Gln Gly Gly
1               5

<210> SEQ ID NO 101
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = beta alanine
<222> LOCATION: (2)..(2)
<220> FEATURE:
<221> NAME/KEY: Xaa = beta alanine
<222> LOCATION: (4)..(4)
<220> FEATURE:
<221> NAME/KEY: Xaa = beta alanine
<222> LOCATION: (6)..(6)
<220> FEATURE:
<221> NAME/KEY: Xaa = beta alanine
<222> LOCATION: (8)..(8)
<220> FEATURE:
<221> NAME/KEY: Xaa = beta alanine
<222> LOCATION: (10)..(10)
<220> FEATURE:
```

```
<221> NAME/KEY: Xaa = beta alanine
<222> LOCATION: (12)..(12)
<220> FEATURE:
<221> NAME/KEY: Xaa = beta alanine
<222> LOCATION: (14)..(14)
<220> FEATURE:
<221> NAME/KEY: Xaa = beta alanine
<222> LOCATION: (16)..(16)

<400> SEQUENCE: 101

Glu Xaa Lys Xaa Glu Xaa Lys Xaa Glu Xaa Lys Xaa Glu Xaa Lys Xaa
1               5                   10                  15

<210> SEQ ID NO 102
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = beta alanine
<222> LOCATION: (2)..(2)
<220> FEATURE:
<221> NAME/KEY: Xaa = beta alanine
<222> LOCATION: (4)..(4)
<220> FEATURE:
<221> NAME/KEY: Xaa = beta alanine
<222> LOCATION: (6)..(6)
<220> FEATURE:
<221> NAME/KEY: Xaa = beta alanine
<222> LOCATION: (8)..(8)

<400> SEQUENCE: 102

Glu Xaa Lys Xaa Glu Xaa Lys Xaa
1               5

<210> SEQ ID NO 103
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = beta alanine
<222> LOCATION: (2)..(2)
<220> FEATURE:
<221> NAME/KEY: Xaa = beta alanine
<222> LOCATION: (4)..(4)
<220> FEATURE:
<221> NAME/KEY: Xaa = beta alanine
<222> LOCATION: (6)..(6)
<220> FEATURE:
<221> NAME/KEY: Xaa = beta alanine
<222> LOCATION: (8)..(8)
<220> FEATURE:
<221> NAME/KEY: Xaa = beta alanine
<222> LOCATION: (10)..(10)
<220> FEATURE:
<221> NAME/KEY: Xaa = beta alanine
<222> LOCATION: (12)..(12)
<220> FEATURE:
<221> NAME/KEY: Xaa = beta alanine
<222> LOCATION: (14)..(14)
<220> FEATURE:
<221> NAME/KEY: Xaa = beta alanine
<222> LOCATION: (16)..(16)

<400> SEQUENCE: 103

Arg Xaa Asp Xaa Arg Xaa Asp Xaa Arg Xaa Asp Xaa Arg Xaa Asp Xaa
1               5                   10                  15

<210> SEQ ID NO 104
<211> LENGTH: 8
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = beta alanine
<222> LOCATION: (2)..(2)
<220> FEATURE:
<221> NAME/KEY: Xaa = beta alanine
<222> LOCATION: (4)..(4)
<220> FEATURE:
<221> NAME/KEY: Xaa = beta alanine
<222> LOCATION: (6)..(6)
<220> FEATURE:
<221> NAME/KEY: Xaa = beta alanine
<222> LOCATION: (8)..(8)

<400> SEQUENCE: 104

Arg Xaa Asp Xaa Arg Xaa Asp Xaa
1               5
```

SELF-ASSEMBLING PEPTIDE GEL FORMULATION AND METHODS OF USE

CROSS-REFERENCE TO RELATED APPLICATIONS

This application claims the benefit of and priority to U.S. Provisional Application No. 62/960,550 filed Jan. 13, 2020, and U.S. Provisional Application No. 63/063,704 filed Aug. 10, 2020, which are hereby incorporated by reference in their entirety.

REFERENCE TO SEQUENCE LISTING

The Sequence Listing submitted Jan. 13, 2021, as a text file named "CNS_112_ST25.txt," created on Jan. 4, 2021, and having a size of 29,159 bytes is hereby incorporated by reference pursuant to 37 C.F.R. § 1.52(e) (5).

FIELD OF THE INVENTION

The invention is generally directed to compositions of self-assembling peptides and self-assembling peptidomimetics and methods for use in creating tissue, and as a bulking agent or a lift in conjunction with a procedure, which may be surgical, laparoscopic or injection.

BACKGROUND OF THE INVENTION

Minimally invasive approaches to medical procedures can lessen adverse effects, pain, recovery time, duration of stay and costs, while improving outcomes when compared to more invasive approaches. For example, gastrointestinal tumor and polyp resections previously treated by traditional open surgery are typically now performed laparoscopically, and where possible, endoscopically. Improved clinical techniques and advances in technology that address a wider array of diseases and injuries have supported the trend toward less invasiveness, but further advances in tools are required as many needs of clinicians remain unmet. For example, endoscopy can be used to detect, visualize, examine, biopsy and resect small and large lesions in gastrointestinal mucosa. Endoscopic resection techniques have gradually improved and gained more importance in the management of premalignant and malignant lesions of the digestive tract. Endoscopic resection techniques include, for instance, polypectomy, endoscopic mucosal resection (EMR) and endoscopic submucosal dissection (ESD). Such procedures, especially ESD, require a high degree of training and skill.

Submucosal injection is common during EMR and is integral to ESD. In order to improve the efficiency, operability and safety of such procedures, a cushion, also known as a lift, is conventionally produced beneath the tissue or lesion that is targeted for resection, dissection or repair in order to elevate and separate it from the underlying tissue. While saline is often used for this purpose, its utility is constrained because the resulting cushion is easily deformed and possesses a limited degree of lift and durability. Newer materials, including some that are polymer-based, have short periods of efficacy and must be re-administered if the procedure exceeds thirty minutes to two hours.

To attempt to overcome some of the drawbacks associated with normal saline, several solutions have been developed, including submucosal injection of glucose solution, glycerol, sodium hyaluronate, colloids, hydroxypropyl methylcellulose, fibrinogen solution, ELEVIEW®, and ORISE™ gel (Castro, R. et al., World J Gastroenterol., 25 (7): 777-788 (2019)). However, these solutions also possess disadvantages. They can be difficult to prepare or administer, may not be readily available, may be expensive, may damage or hinder tissue repair and wound healing, can impair histological assessment, and can be associated with toxicity. Furthermore, they produce cushions that do not last sufficiently long, often requiring multiple cumbersome injections that raise the risk of error and injury. Additionally, these approaches do not treat or prevent bleeding, perforation or inflammation, which are common complications of EMR and ESD, or provide a seal to tissue that has been sutured or clipped. Bleeding can interfere with subsequent procedures, impair the clinician's field of vision, lead to hematomas and seromas, lead to morbidity or mortality, and make procedures, such as ESD, more time consuming and inefficient.

Tools that better address these and other problems are needed.

Therefore, it is an object of the present invention to provide biocompatible, injectable compositions to enable better separation of tissues and visualization of margins, more durable and robust lifts, less need for frequent injections that carry risk of undesired perforation, and simultaneous management of adverse effects, such as bleeding, leaking and inflammation during endoscopic, laparoscopic or otherwise minimally invasive, or open surgical procedures in and/or on the body.

SUMMARY OF THE INVENTION

Formulations of self-assembling peptides or peptidomimetics, or combinations thereof, referred to herein jointly as self-assembling peptides unless otherwise specified, can be used to create a long-lasting "lift" or means of elevating tissue to be resected, dissected, manipulated or repaired, as a bulking agent, or as a tissue-forming matrix by injection of a solution that forms a solid gel in situ, which is stable for a prolonged period of time from days to a month, is hemostatic, and may prevent adhesions. Examples demonstrate these formulations and methods of use thereof enable better separation of tissues and visualization of margins, more durable and robust lifts, less need for frequent injections that carry risk of undesired perforation, and simultaneous management of adverse effects, such as bleeding, leaking, inflammation and iatrogenic injury during endoscopic, laparoscopic or other minimally invasive, or open surgical procedures in and/or on the body An example includes a composition containing self-assembling peptides that is administered to form a durable submucosal lift and tunnel with margin visualization, bleeding control, perforation prophylaxis, and/or isolation from vital structures during gastrointestinal EMR and ESD and methods of use thereof. Such compositions are useful at a target site encompassing a lesion that is to be resected, dissected, manipulated or repaired during an endoscopic, laparoscopic or otherwise minimally invasive, or open surgical procedure. The compositions not only provide an effective lift or bulking agent effective for at least one, two, three or four hours, up to two to four weeks, but are also hemostatic, can be effective as a barrier to liquid or gas, and may reduce formation of adhesions at the site. The composition has a further advantage in that it provides a seal to a surgical wound in gastrointestinal tissue in combination with, or without, sutures, clips or other devices.

Compositions of self-assembling peptides and methods of use in endoscopic procedures and for injection are described. These are provided in an effective amount to form a cushion or lift at or enable tunneling beneath a target site, in an effective amount to create new tissue, or as a bulking agent. The compositions are typically provided in the form of a pre-filled syringe, most commonly having a volume of between one and ten mL, such as 1, 2, 5, or 10 mL. In some embodiments, the compositions include one or more therapeutic agents, prophylactic agents, and/or diagnostic or imaging agents, such as dyes or radiopaque compounds. In preferred embodiments, the compositions contain a dye, such as, but not limited to methylene blue, indigo carmine or a food coloring, or a radiopaque material.

Typically, the composition is administered at or below a target site to form a lift that is positioned and of desired height and/or shape to facilitate resection of a lesion or for the purpose of tunneling through the submucosa below the lesion prior to resection. A typical approximate volume of 1 to 5 mL of composition is used to elevate a polyp, but larger polyps may require at least 10 mL. Even larger lesions or long tunnels may require volumes of 15-20 mL and potentially more. The composition can be used to elevate and isolate a lesion such as polyp or tumor, including mesenchymal tumors, lymphomas, epithelial tumors, and gastrointestinal stromal tumors, among others. Lesions may also include inflammatory tissue, pseudo-polyps, serrated lesions, adenomas, ulcerations, dysplasias, pre-neoplastic and neoplastic formations, and congenital abnormalities. The duration of the lift provided by the composition of self-assembling peptides may vary. In some embodiments, the cushion or lift lasts for at least 30 minutes, such as up to 12 hours or more, but it is important only that the lift lasts for the duration of the procedure.

The formulations can be injected to smooth wrinkles or scars or for other plastic surgery indications. The formulations can also be used to create tissue, for example, to raise the neck of the urethra to prevent bladder leakage.

In some embodiments, the self-assembling peptides self-assemble to form a barrier structure that prevents or reduces movement of one or more bodily fluids (e.g., blood, serum, gastrointestinal lumen contents) through the structure. Self-assembly is induced upon contact of the self-assembling peptides with one or more bodily fluids (e.g., blood, serum) present at the target site. In some embodiments, the elf-assembling peptides may be formulated to be at least partially self-assembled prior to application to the target site (e.g., tissue). In some embodiments, the compositions applied to a target site, for example, before, during, and/or after the procedure (e.g., the resection) are hemostatic and/or may prevent or reduce the movement of one or more bodily fluids. In some embodiments, the hemostatic effect is prophylactic. In some embodiments, the composition reduces time to hemostasis at or near the target site and/or lesion, for example, by at least about 10%, at least about 30%, at least about 50%, or at least about 75%, relative to the time of hemostasis in the absence of the composition.

Studies conducted included use of a self-assembling peptide formulation, such as $(RADA)_4$ self-assembling peptide formulation, that is typically at least 75 weight percent ("%"), 80%, 85% or 90% self-assembling peptide and the remainder inert vehicle such as sterile water, which is formulated in a prefilled syringe, either as a dry powder for reconstitution or a solution, and with or without a visualizing agent such as a dye. When applied, the self-assembling peptides locally assemble into an extracellular matrix-like scaffold due to exposure to ions. The results confirm that uses of the formulations include 1) creating cushions for EMR; 2) tunnels with better margin visualization in ESD and 3) providing concomitant hemostasis by virtue of forming a contiguous physical-mechanical seal with the wound bed/tissue, in both gastrointestinal as well as tumor models in swine. The resulting microenvironment is conducive to tissue repair and wound healing, and therefore establish that the product can be used as a bulking agent or to create tissue. The self-assembling peptide gel typically persists for at least two to four weeks.

DETAILED DESCRIPTION OF THE INVENTION

I. Definitions

Use of the term "about" is intended to describe values either above or below the stated value in a range of approx. +/−10%; in other embodiments the values may range in value either above or below the stated value in a range of approximately +/−5%.

"Biocompatible" refers to compatibility with living tissue or a living system by not being toxic, injurious, or physiologically reactive and not causing immunological rejection. A biocompatible material, along with any metabolites or degradation products thereof are generally non-toxic to the recipient and do not cause any significant adverse effects to the recipient. Biocompatible materials are generally materials which do not elicit a significant or problematic inflammatory or immune response when administered to a patient.

"Biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks. Degradation can include disassembly of self-assembled peptide structures. Therefore, in some embodiments, degradation can include disassembly of self-assembled structures.

"Self-assembling" refers to the spontaneous or induced assembly of molecules into defined, stable, non-covalently bonded structures that are held together by intermolecular and/or intramolecular forces.

"Effective amount", in reference to a therapeutic, prophylactic and/or diagnostic or imaging agent or vehicle such as a self-assembling peptide formulation, is a dosage necessary to elicit a desired response. The effective amount of an agent may vary depending on such factors as the desired biological endpoint, the agent to be delivered, the nature of the site to which the agent is delivered, the nature of the conditions for which the agent is administered, etc. For example, the effective amount of a composition for hemostasis may be an amount sufficient to promote hemostasis to a greater extent than would occur in the absence of the composition.

"Minimally Invasive" and "Minimally Invasively" refers to a procedure in which access to the tissue, organ, or body is made with tools or techniques that minimize or limit the required size and/or number of incisions. Examples include, but are not limited to, arthroscopic, hysteroscopic, laparoscopic, percutaneous, endoscopic, and natural orifice transluminal endoscopic procedures.

"Preventing" refers to causing a condition, state, disease, symptom or manifestation of such, or worsening of the severity of such, not to occur. Preventing includes reducing the risk that a condition, state, disease, or symptom or manifestation of such, or worsening of the severity of such, will occur.

"Treat", "treatment" and "treating" refer to the reduction or amelioration of the progression, severity and/or duration of one or more symptoms of an injury, disease or disorder, delay of the onset of a disease or disorder, or the amelioration of one or more consequences, indications or symptoms (preferably, one or more discernible symptoms) of an injury, disease or disorder, resulting from the administration of one or more therapies (e.g., one or more therapeutic agents such as a compound as described). The terms "treat", "treatment", and "treating" also encompass the reduction of the risk of developing a disease or disorder, and the delay or inhibition of the recurrence of a disease or disorder.

"Small Molecule" refers to a molecule having a relatively low molecular weight, such as less than about 1000 or 1,500 g/mol. Typically, small molecules are not peptides or nucleic acids.

"Surgery" and "Surgical", unless otherwise specified, refer to treating injuries, diseases, deformities and/or undesirable features of, in, or on the body by the physical removal, repair, or readjustment of organs and/or tissues, often involving cutting into the body, regardless of whether performed as a minimally invasive or traditional open procedure.

II. Formulations

The compositions typically contain one or more self-assembling peptides in an effective amount to form a cushion or lift at a target site. In some embodiments, mixtures of self-assembling peptides may be used.

The compositions are formulated for administration into one or more internal structures by injection. Typically, the assembly of the self-assembling peptides is initiated upon contact with physiological fluids. Therefore, in some embodiments, compositions of substantially non-assembled self-assembling peptides are induced to assemble in vivo upon administration into a target site in the body (e.g., upon contact with blood, serum, pus, or other bodily fluids, extracellular fluid or interstitial fluid).

A. Self-Assembling Peptides and Peptidomimetics (SAP)

The compositions include one or more self-assembling peptides and/or peptidomimetics (i.e., peptides having a sequence of amino acid residues that are capable of self-assembly). Suitable peptides and peptidomimetics are described in U.S. Pat. Nos. 9,415,084 and 9,789,157. The preferred self-assembling peptides are manufactured by Arch Biosurgery.

The term "peptide" includes "polypeptide," "oligopeptide," and "protein," and refers to a chain of at least two α-amino acid residues linked together by covalent bonds (peptide bonds). The D-enantiomer ("D-α-amino acid") of residues may also be used. When D-α-amino acid residues (Xaa) are included within a sequence, they are annotated as "XaaD".

Peptides can be represented as amino acid residue sequences. Those sequences are written left to right in the direction from the amino ("N—") to the carboxyl ("—C") terminus. In accordance with standard nomenclature, amino acid residue sequences are denominated by either a three letter or a single letter.

"Variant" refers to a polypeptide that differs from a reference polypeptide but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity.

Substitution of like amino acids can also be made on the basis of hydrophilicity, particularly where the biological functional equivalent polypeptide or peptide thereby created is intended for use in immunological embodiments. Amino acid substitutions are generally based on the relative similarity of the amino acid side-chain substituents, for example, their hydrophobicity, hydrophilicity, charge, and size.

In some embodiments the self-assembling peptides have a sequence of amino acid residues conforming to one or more of the following formulas:

$$((Xaa^{neu}-Xaa^+)_x(Xaa^{neu}-Xaa^-)_y)_n \qquad (I)$$

$$((Xaa^{neu}-Xaa^-)_x(Xaa^{neu}-Xaa^+)_y)_n \qquad (II)$$

$$((Xaa^+-Xaa^{neu})_x(Xaa^--Xaa^{neu})_y)_n \qquad (III)$$

$$((Xaa^--Xaa^{neu})_x(Xaa^+-Xaa^{neu})_y)_n \qquad (IV)$$

$$Xaa^{neu}((Xaa^{neu}-Xaa^+)_x(Xaa^{neu}-Xaa^-)_y)_n \qquad (V)$$

$$Xaa^{neu}((Xaa^{neu}-Xaa^-)_x(Xaa^{neu}-Xaa^+)_y)_n \qquad (VI)$$

$$((Xaa^+-Xaa^{neu})_x(Xaa^--Xaa^{neu}neu)_y)_nXaa^{neu} \qquad (VII)$$

$$((Xaa^--Xaa^{neu})_x(Xaa^+-Xaa^{neu})_y)_nXaa^{neu} \qquad (VIII)$$

$$((Xaa^{neu}-Xaa^+)_x(Xaa^{neu}-Xaa^-)_y)_nXaa^{neu} \qquad (IX)$$

$$((Xaa^{neu}-Xaa^-)_x(Xaa^{neu}neu-Xaa^+)_y)_nXaa^{neu} \qquad (X)$$

$$Xaa^{neu}((Xaa^+-Xaa^{neu})_x(Xaa^--Xaa^{neu})_y)_n \qquad (XI)$$

$$Xaa^{neu}((Xaa^--Xaa^{neu})_x(Xaa^+-Xaa^{neu})_y)_n \qquad (XII)$$

where each $Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2, 3, or 4, independently; and n is an integer having a value of 1-5. In preferred embodiments, the one or more SAP are or include RADARADARADARADA (RADA16 or (RADA)$_4$; SEQ ID NO:1).

In a preferred embodiment, most of the self-assembling peptides in the composition are of the same size and have the same amino acid sequence. For example, 75% or more, such as 80%, 85%, 90%, 95%, or 99% of the self-assembling peptides are of the same size and have the same amino acid sequence. The concentration of self-assembling peptides typically is between about 0.1% weight/volume (w/v) and about 6% w/v, inclusive, preferably between about 0.1% w/v and about 4% w/v, inclusive, more preferably between about 1% w/v and about 3% w/v, inclusive. In certain embodiments, the concentration of ions in the formulation, prior to administration, is less than 10 mM, preferably less than 5 mM, and more preferably between 5 nM and 5 mM.

The self-assembling peptides can vary in length so long as they retain the ability to self-assemble to an extent useful for one or more of the desired purposes. Typically, peptides which self-assemble have from about 4 to about 64 residues, more preferably from about 8 to about 36 residues, most preferably from about 8 to about 16 residues. In preferred embodiments, the peptide has from about 8 to about 12 residues, or about 12 to about 16 residues, or about 16 to about 20 residues.

The self-assembling peptides can have an amphiphilic nature (e.g., the peptides can contain, but do not require, approximately equal numbers of hydrophobic and hydrophilic amino acid residues) and are complementary and structurally compatible. "Complementary" means having the capability of forming ionic or hydrogen bonding interactions between hydrophilic residues from adjacent peptides in a structure. Each hydrophilic residue in a peptide either hydrogen bonds or ionically pairs with a hydrophilic residue on an adjacent peptide, or is exposed to solvent. Pairing may also involve van der Waals forces.

The side chains (or R groups) of self-assembling peptides can partition into two faces, a polar face with positively and/or negatively charged ionic side chains (e.g., side chains containing —OH, —NH, —CO$_2$H, or —SH groups), and a nonpolar face with side chains that are considered neutral or uncharged at physiological pH (e.g., the side chain of an alanine residue or residues having other hydrophobic groups). The positively charged and negatively charged amino acid residues on the polar face of one peptide can form complementary ionic pairs with oppositely charged residues of another peptide. These peptides are referred to as ionic, self-complementary peptides. If the ionic residues alternate with one positively and one negatively charged residue on the polar face (−+−+−+−+), the peptides may be described as "modulus I;" if the ionic residues alternate with two positively and two negatively charged residues (−−++−−++) on the polar face, the peptides are described as "modulus II;" if the ionic residues alternate with three positively and three negatively charged residues (+++−−−+++−−−) on the polar face, the peptides are describe as "modulus III;" if the ionic residues alternate with four positively and four negatively charged residues (++++−−−−++++−−−−) on the polar face, they are described as "modulus IV." For example, a peptide having four repeating units of the sequence EAKA (SEQ ID NO: 77) may be designated EAKA16-I, and a peptide having four repeating units of the sequence RADA (SEQ ID NO: 57) may be designated RADA16-I. Peptides having other sequences may be described by the same convention.

Hydrophilic residues typically contain a polar functional group or a functional group that is charged at physiological conditions. Exemplary charged or polar functional groups include, but are not limited to, carboxylic acid groups, amino groups, sulfate groups, hydroxyl groups, halogen groups, nitro groups, phosphate groups, etc. Hydrophobic residues are those residues that contain non-polar functional groups.

Exemplary non-polar functional groups include, but are not limited to, alkyl groups, alkene groups, alkyne groups, and phenyl groups.

In one embodiment, the hydrophilic residue has the formula —NH—CH(X)—COO—, wherein X has the formula $(CH_2)_y Z$, wherein y=0-8, preferably 1-6, more preferably 1-4, and most preferably 1-3, and Z is a polar or charged functional group including, but not limited to, a carboxylic acid group, an amino group, a sulfate group, a hydroxyl group, a halogen group, a nitro group, a phosphate group, or a functional group containing a quaternary amine. The alkyl chain can be in a linear, branched, or cyclic arrangement. X may also contain one or more heteroatoms within the alkyl chain and/or X may be substituted with one or more additional substituents. In a preferred embodiment, Z is a carboxylic acid group or an amino group. In one embodiment, the hydrophobic residue has the formula-NH—CH(X)—COO—, wherein X has the formula $(CH_2)_y Z$, wherein y=0-8, preferably 1-6, more preferably 1-4, and more preferably 1-3, and Z is a non-polar functional group including, but not limited to, an alkyl group, an alkene group, an alkyne group, or a phenyl group. The alkyl, alkene, or alkyne chain can be in a linear, branched, or cyclic arrangement. X may also contain one or more heteroatoms within the alkyl chain and/or X may be substituted with one or more additional substituents. In a preferred embodiment, X is an alkyl group, such as a methyl group.

Other hydrophilic residues that form hydrogen bonds including, but not limited to, asparagine and glutamine, may be incorporated into the peptides. If the alanine residues in the peptides are changed to more hydrophobic residues, such as leucine, isoleucine, phenylalanine or tyrosine, the resulting peptides have a greater tendency to self-assemble and form peptide matrices with enhanced strength.

In one embodiment, the self-assembling peptides have a sequence of amino acid residues conforming to one or more of Formulas I-XII:

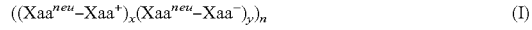  (I)

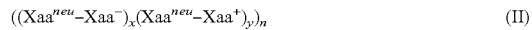  (II)

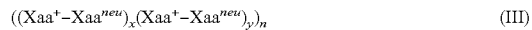  (III)

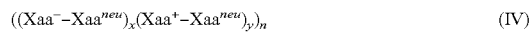  (IV)

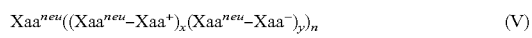  (V)

  (VI)

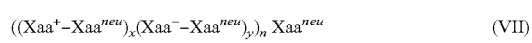  (VII)

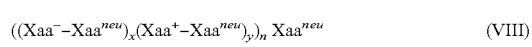  (VIII)

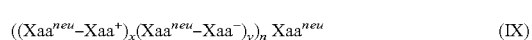  (IX)

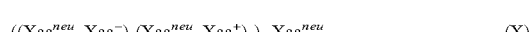  (X)

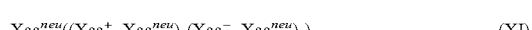  (XI)

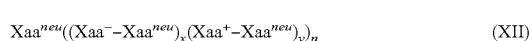  (XII)

wherein each $Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2, 3, or 4, independently; and n is an integer having a value of 1-5. The charge (e.g., neutral, positive or negative) can be the charge at physiological conditions (e.g., pH).

Useful peptides can also include one or more amino acid residues having a neutral charge between one or more sets of residues conforming to any one of Formulas I-IV. For example, in some embodiments, peptides include sequences conforming to Formulas III and IV, linked with a single amino acid residue having a neutral charge, or linked with two amino acid residues having a neutral charge, or linked with three amino acid residues having a neutral charge.

Peptides with modulus I (i.e., peptides having alternate positively and negatively charged R groups on one side (e.g., the polar face of the β-sheet) are described by each of Formulas I-IV, where x and y are 1. Examples of peptides of modulus I include, but are not limited to, RADA (SEQ ID NO: 57) and RADARADARADARADA (SEQ ID NO: 1). Examples of peptides of modulus II (i.e., peptides having two residues bearing one type of charge (e.g., a positive charge) followed by two residues bearing another type of charge (e.g., a neutral charge)) are described by the same formulas where both x and y are 2. Examples of peptides of modulus III (i.e., peptides having three residues bearing one type of charge (e.g., a positive charge) followed by three residues bearing another type of charge (e.g., a negative charge)) include, but are not limited to, RARARADADADA (SEQ ID NO: 93). Examples of peptides of modulus IV (i.e., peptides having four residues bearing one type of charge (e.g., a positive charge) followed by four residues bearing another type of charge (e.g., a negative charge)) include, but are not limited to, RARARARADADADADA (SEQ ID NO: 94).

In some embodiments, the self-assembling peptides include two or more repeating units of the sequence RADA (SEQ ID NO: 57), two or more repeating units of the sequence EAKA (SEQ ID NO: 77), or combinations thereof.

In some embodiments, SAP include one or more segments of positively or negatively charged residues (under physiological conditions). For example, these segments can include a sequence of positively or negatively charged residues, for example, about 2 to about 50 amino acid residues, typically about 3 to about 30 residues, more typically about 10 to about 20 amino acid residues. In some embodiments, about half of the residues of a self-assembling peptides can be positively charged and about half of the residues can be negatively charged. For example, self-assembling peptides can have the following sequence RRRRDDDD (SEQ ID NO: 95) or GGGGSSSS (SEQ ID NO: 96). In some embodiments, self-assembling peptides contain sequences in which at least one hydrophobic residue alternates with at least one hydrophilic residue (under physiological conditions). For example, the sequence of a representative self-assembling peptide can be one or more units of GQGQ (SEQ ID NO: 97), GGQQGG (SEQ ID NO: 98), GQQGQQG (SEQ ID NO: 99), GGQGGQGG (SEQ ID NO: 100), etc.

Other exemplary peptides that can be used are described in U.S. Pat. Nos. 5,670,483; 5,955,343; 6,548,630; 6,800,481; 7,098,028; 9,327,010; and 9,364,513 to Zhang, et al.; U.S. Pat. Nos. 9,162,005; 9,415,084; and 9,339,476 to Ellis-Behnke, et al.; Holmes, et al., *Proc. Natl. Acad. Sci. USA*, 97:6728-6733 (2000); Zhang, et al., *Proc. Natl. Acad. Sci. USA*, 90:3334-3338 (1993); Zhang, et al., *Biomaterials*, 16:1385-1393 (1995); Caplan et al., *Biomaterials*, 23:219-227 (2002); Leon, et al., *J. Biomater. Sci. Polym. Ed.*, 9:297-312 (1998); and Caplan, et al., *Biomacromolecules*, 1:627-631 (2000).

The compositions can include a mixture of one or more peptides. Peptide-based structures can be formed of heterogeneous mixtures of peptides (i.e., mixtures containing more than one type of peptide conforming to a given formula or to two or more of the formulas). In some embodiments, each type of peptide in the mixture can self-assemble with the same type of peptide. In other embodiments, one or more of each type of peptide would not self-assemble alone, but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides, which are complementary and structurally compatible to each other, can be used.

One or more short amino acid sequences that assists in self-assembly (referred to as assembly assist sequences) can be added to a homogeneous or heterogeneous mixture of amino acid sequences that alone do not self-assemble. The assembly assist sequences contain amino acids that are complementary with the amino acids in the sequences in the mixture. The assembly assist sequences may contain any number of amino acids. Preferably, the assembly assist sequences contain at least four amino acids. The assembly assist sequences may contain a flexible linker (e.g., PEG, N-succinimidyl 3-(2-pyridyldithio) propionate) between the amino acids that assist in self-assembly. For example, the assembly assist sequence may contain a pair, a triad, or a quartet of assembly assisting amino acids at the termini of the sequence which are connected via a flexible linker. Suitable assembly assist sequences include, but are not limited to, RADA (SEQ ID NO: 57) and EAKA (SEQ ID NO: 77).

Self-assembling peptides structures can have varying degrees of stiffness or elasticity. The structures typically have a low elastic modulus (e.g., a modulus in the range of between about 0.01 and about 1,000 kPa, preferably between about 1 and about 100 kPa, more preferably between about 1 and about 10 kPa as measured by standard methods, such as in a standard cone-plate rheometer. Low values may be preferable, as they permit structure deformation as a result of movement, in response to pressure. Stiffness can be controlled in a variety of ways, including by changing the length, sequence, and/or concentration of the self-assembling peptide precursors. Other methods for increasing stiffness can also be employed. For example, one or more cysteine residues may be incorporated into the peptides, and these residues may bond with one another through the formation of disulfide bonds. Structures bonded in this manner may have increased mechanical strength relative to structures made with comparable peptides that do not include cysteine residues and thus are unable to form disulfide bonds. As another example, one can attach to the self-assembling peptides precursors, either biotin or other molecules that can be subsequently cross-linked or otherwise bonded to one another. One or more physical, mechanical, and/or chemical crosslinkers can be incorporated. The crosslinks can serve to reinforce the material or to provide increased rigidity, strength and/or half-life (e.g., in vivo half-life). Modified (i.e., functionalized) or unmodified polyethylene glycol (PEG) can be used.

Crosslinkers such as biotin can be included at an N- or C-terminus of a peptide or attached to one or more residues between the termini. Other suitable cross-linkers including, for example, amino acid residues with polymerizable groups such as vinyl groups, may be incorporated and cross-linked by exposure to UV light. The extent of crosslinking can be precisely controlled by applying the radiation for a predetermined length of time. The extent of crosslinking can be determined by light scattering, gel filtration, scanning electron microscopy, or other methods well known in the art. Crosslinking can be assessed by HPLC or mass spectrometry analysis of the structure after digestion with a protease, such as a matrix metalloprotease. Material strength may be determined before and/or after cross-linking.

Factors influencing the physical properties of self-assembled peptide structures include, but are not limited to, peptide sequence, peptide length, presence of bound agents, the amount of peptide (e.g., concentration, mass and volume), peptide form (e.g., powder, solution, or gel) and assembly-state at application time.

The structures formed from self-assembling peptides made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in the peptide structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade.

Typically, the self-assembling peptides are biocompatible, non-toxic, fully or partially biodegradable, and do not cause local or systemic inflammation. Preferably, breakdown products of the self-assembling peptides do not cause secondary toxicity and are suitable for growth and repair of the surrounding tissues.

Exemplary Self-Assembling Sequences

The following table provides a non-limiting list of self-assembling sequences that may be used in accordance with the present disclosure.

TABLE 1

Representative Self-Assembling Peptide Sequences

| Sequence (N → C) | SEQ ID NO: |
| --- | --- |
| RADARADARADARADA | 1 |
| SGSGSGSGSGSGSGSG | 2 |
| SASASASASASASASA | 3 |
| SVSVSVSVSVSVSVSV | 4 |
| SLSLSLSLSLSLSLSL | 5 |
| SISISISISISISISI | 6 |
| SMSMSMSMSMSMSMSM | 7 |
| SFSFSFSFSFSFSFSF | 8 |
| SWSWSWSWSWSWSWSW | 9 |
| SPSPSPSPSPSPSPSP | 10 |

TABLE 1-continued

Representative Self-Assembling Peptide Sequences

| Sequence (N → C) | SEQ ID NO: |
| --- | --- |
| TGTGTGTGTGTGTGTG | 11 |
| TATATATATATATATA | 12 |
| TVTVTVTVTVTVTVTV | 13 |
| TLTLTLTLTLTLTLTL | 14 |
| TITITITITITITITI | 15 |
| TMTMTMTMTMTMTMTM | 16 |
| TFTFTFTFTFTFTFTF | 17 |
| TWTWTWTWTWTWTWTW | 18 |
| TPTPTPTPTPTPTPTP | 19 |
| CGCGCGCGCGCGCGCG | 20 |
| CACACACACACACACA | 21 |
| CVCVCVCVCVCVCVCV | 22 |
| CLCLCLCLCLCLCLCL | 23 |
| CICICICICICICICI | 24 |
| CMCMCMCMCMCMCMCM | 25 |
| CFCFCFCFCFCFCFCF | 26 |
| CWCWCWCWCWCWCWCW | 27 |
| CPCPCPCPCPCPCPCP | 28 |
| YGYGYGYGYGYGYGYG | 29 |
| YAYAYAYAYAYAYAYA | 30 |
| YVYVYVYVYVYVYVYV | 31 |
| YLYLYLYLYLYLYLYL | 32 |
| YIYIYIYIYIYIYIYI | 33 |
| YMYMYMYMYMYMYMYM | 34 |
| YFYFYFYFYFYFYFYF | 35 |
| YWYWYWYWYWYWYWYW | 36 |
| YPYPYPYPYPYPYPYP | 37 |
| NGNGNGNGNGNGNGNG | 38 |
| NANANANANANANANA | 39 |
| NVNVNVNVNVNVNVNV | 40 |
| NLNLNLNLNLNLNLNL | 41 |
| NINININININININI | 42 |
| NMNMNMNMNMNMNMNM | 43 |
| NFNFNFNFNFNFNFNF | 44 |
| NWNWNWNWNWNWNWNW | 45 |
| NPNPNPNPNPNPNPNP | 46 |
| QGQGQGQGQGQGQGQG | 47 |

TABLE 1-continued

Representative Self-Assembling Peptide Sequences

| Sequence (N → C) | SEQ ID NO: |
|---|---|
| QAQAQAQAQAQAQAQA | 48 |
| QVQVQVQVQVQVQVQV | 49 |
| QLQLQLQLQLQLQLQL | 50 |
| QIQIQIQIQIQIQIQI | 51 |
| QMQMQMQMQMQMQMQM | 52 |
| QFQFQFQFQFQFQFQF | 53 |
| QWQWQWQWQWQWQWQW | 54 |
| QPQPQPQPQPQPQPQP | 55 |
| AEAKAEAKAEAKAEAK | 56 |
| RADA | 57 |
| RAEARAEARAEARAEA | 58 |
| KADAKADAKADAKADA | 59 |
| ARADARADARADA | 60 |
| RADARADARADARADARADA | 61 |
| ARADARADARADARADARADA | 62 |
| ARADARADARADARADA | 63 |
| RLDLRLDLRLDLRLDL | 64 |
| RLDL | 65 |
| RLDLRL | 66 |
| RADARA | 67 |
| LRLDLR | 68 |
| IEIKIEIKIEIKI | 69 |
| IEIKIEIKIEIKIEIK | 70 |
| IEIKIEIKIEIKIEIKI | 71 |
| IEIKIEIKIEIKIEIKIEIK | 72 |
| IEIKIEIKIEIKIEIKIEIKI | 73 |
| IEIKIEIKIEIK | 74 |
| EIKIEIKIEIKIEIKI | 75 |
| EAKAEAKAEAKAEAKA | 76 |
| EAKA | 77 |
| EAKAEAKAEA | 78 |
| EAKAEAKAEAKAEAKAEAKA | 79 |
| AEAKAEAKAEAKAEAKA | 80 |
| AEAKAEAKAEAKA | 81 |
| RADARADARADARADARA | 82 |
| R$^D$A$^D$D$^D$A$^D$R$^D$A$^D$D$^D$A$^D$R$^D$A$^D$D$^D$A$^D$R$^D$A$^D$D$^D$A$^D$ | 83 |
| R$^D$A$^D$D$^D$A$^D$R$^D$A$^D$D$^D$A$^D$R$^D$A$^D$D$^D$A$^D$ | 84 |
| E$^D$A$^D$K$^D$A$^D$E$^D$A$^D$K$^D$A$^D$E$^D$A$^D$K$^D$A$^D$ | 85 |
| E$^D$A$^D$K$^D$A$^D$ | 86 |
| R$^D$A$^D$D$^D$A$^D$ | 87 |
| RADARADA | 88 |
| EARAEARAEARAEARA | 89 |
| EARAEARAEARA | 90 |
| EARAEARAE | 91 |
| EARA | 92 |

Self-assembling peptides can be generated which differ from those explicitly exemplified in Table 1 by a single amino acid residue or by multiple amino acid residues (e.g., by inclusion or exclusion of a repeating quartet, or 1, 2, 3, 4, 5 or more residues). The single or multiple amino acid residues may be included or excluded at the N- and/or C-termini of the peptides. The single or multiple amino acid residues may be neutral or charged (i.e., positive or negative) at physiological pH.

Peptide Modifications

The peptides may be modified in various ways. In some embodiments, the modification(s) may render the peptides more stable (e.g., resistant to degradation in vivo). Useful modifications include, without limitation, chemical modification, N terminus modification, C terminus modification, peptide bond modification, backbone modifications, residue modification, D-amino acids, or non-natural amino acids or others. An individual peptide may contain one or more modifications.

Incorporation of artificial or non-natural amino acids are contemplated, Non-naturally occurring amino acids are not found or have not been found in nature, but they can by synthesized and incorporated into a peptide chain. Non-natural amino acids are known to those skilled in the art of chemical synthesis and peptide chemistry. Non-limiting examples of suitable non-natural amino acids (each one in L- or D-configuration) are azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, and 3-(6-chloroindolyl) alanin.

In some embodiments, peptide bonds (—CO—NH—) within the peptide may be substituted, for example, by N-methylated bonds (—N(CH3)-CO—), ester bonds (—C(R)H—C-0-0-C(R)—N—), ketomethylen bonds (—CO—CH2-), CC-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (e.g., 2, 3, 4 or more) at the same time.

One or more of the amino acid residues in a SAP can be altered or derivatized by the addition of one or more chemical entities including, but not limited to, acyl groups, carbohydrate groups, phosphate groups, farnesyl groups, isofarnesyl groups, fatty acid groups, or a linker which allows for conjugation or functionalization of the peptide. For example, either or both ends of a given peptide can be modified. The carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group (RNH—, where R is an organic group (e.g., an amino group —$NH_2$)) can be used to neutralize an "extra" negative charge that may otherwise be present at the C-terminus (e.g., a charge not resulting from the side chain of the C-terminal amino acid residue). Where an amine is used, the C-terminus bears an amide (—CONHR). The neutralization of charges on a terminus may facilitate self-assembly. One of ordinary skill in the art will be able to select other suitable groups.

In some embodiments, the peptides contain one or more of the following modifications: glycosylation, amidation, acetylation, acylation, alkylation, alkenylation, alkynylation, phosphorylation, sulphorization, hydroxylation, hydrogenation, cyclization, ADP-ribosylation, anchor formation, covalent attachment of a lipid or lipid derivative, methylation, myristylation, pegylation, prenylation, esterification, biotinylation, coupling of farnesyl or ubiquitination, a linker which allows for conjugation or functionalization of the peptide, or a combination thereof.

The term "peptidomimetic", refers to non-natural peptide-like molecules that mimic peptide structure. Typically, a peptidomimetic has the activity of the peptide upon which it is structurally based. For example, peptidomimetics typically retain the ability to produce the same biological effect as and can interact with the biological target of the parent peptide. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). Peptidomimetics may be used to circumvent some of the problems associated with a natural peptide: e.g. stability against proteolysis and poor bioavailability (Vagner J., et al. *Curr. Opin. Chem. Biol.*, 12 (3): 292-296 (2008)). Self-assembling peptidomimetics are molecules that are structurally similar to peptides having a segment of residues having a positive charge under physiological conditions joined to a segment of residues having a negative charge under physiological conditions.

The self-assembling peptidomimetics have general features analogous to self-assembling peptides, such as amphiphilicity. Examples of peptidomimetics that can be used are described in Moore et al., *Chem. Rev.* 101 (12), 3893-4012 (2001), and in WO 2007/142757.

The peptidomimetics can be classified into four categories: α-peptides, β-peptides, γ-peptides, and δ-peptides. Self-assembling peptidomimetics including combinations of more than one of α-amino acids, β-amino acids, γ-amino acids, and δ-amino acids can also be used. For example, self-assembling peptidomimetics can include alpha-amino and beta-amino acid residues (i.e., alpha-beta peptides), alpha-amino and delta-amino acid residues (i.e., alpha-delta peptides), and alpha-amino and gamma-amino acid residues (i.e., alpha-gamma peptides). In an exemplary embodiment, a self-assembling peptidomimetic includes both alpha amino acids (annotated as Xaa) and beta amino acids (annotated as $Xaa^B$). Exemplary self-assembling peptidomimetic sequences include $EA^BKA^BEA^BKA^BEA^BKA^BEA^BKA^B$ (SEQ ID NO: 101), $EA^BKA^BEA^BKA^B$ (SEQ ID NO: 102), $RA^BDA^BRA^BDA^BRA^BDA^BRA^BDA^B$ (SEQ ID NO: 103), and $RA^BDA^BRA^BDA^B$ (SEQ ID NO: 104).

The alpha amino acids can be classical or non-classical alpha amino acids (i.e., L-form or D-form, or combinations thereof). Examples of α-peptide peptidomimetics that can be used include, but are not limited to, N,N'-linked oligoureas, oligopyrrolinones, oxazolidin-2-ones, azatides and azapeptides.

Examples of β-peptides include, but are not limited to, β-peptide foldamers, β-aminoxy acids, sulfur-containing β-peptide analogues, and hydrazino peptides.

Examples of γ-peptides include, but are not limited to, γ-peptide foldamers, oligoureas, oligocarbamates, and phosphodiesters.

Examples of δ-peptides include, but are not limited to, alkene-based δ-amino acids and carbopeptoids, such as pyranose-based carbopeptoids and furanose-based carbopeptoids.

B. Therapeutic, Prophylactic and Diagnostic or Imaging Agents

Therapeutic, prophylactic, and diagnostic agents or imaging agents such as dyes or radiopaque agents can be incorporated into the compositions before or during administration. One or more agents can be added/mixed simultaneously or sequentially with self-assembling peptides. The agent(s) can be covalently or non-covalently coupled to the self-assembling materials, either directly or via an intermediate molecule. Exemplary agents include, but are not limited to, anti-angiogenesis agents, anti-infective agents (e.g., an antibiotic, antibacterial, antiviral, or antifungal agent), immunomodulatory agents such as anti-inflammatory agents (e.g., non-steroidal, steroidal), vasoconstrictors, analgesics, anesthetics, antioxidants, cytokines, cells and combinations thereof. The compositions can contain one or more additional agents in any amount that is effective for a desired purpose. For example, an agent (e.g., an anesthetic agent) can be present in the composition in an amount of about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition.

In one preferred embodiment, an imaging agent is added. The compositions can contain one or more dyes or agents such as barium which are radiopaque. Dyes are widely used in compositions for endoscopic procedures. In particular, in compositions for EMR and/or ESD procedures, dyes function to make the margins of the target lesion, the submucosa, and the physiological structures underlying the mucosa, more visible to the endoscopist such that target lesion can be more easily removed with less risk of damaging the submucosal layer or external muscular wall.

Useful dyes include vital dyes (or absorptive dyes), non-vital dyes (or contrast dyes), and reactive dyes. Vital (or absorptive) dyes, such as Lugol's solution and methylene blue, identify specific epithelial cell types by preferential absorption or diffusion across the cell membrane; non-vital (or contrast) dyes, such as indigo carmine, seep through mucosal crevices and highlight surface topography and mucosal irregularities; reactive dyes, such as congo red and phenol red, undergo chemical reactions with specific cellular constituents, resulting in a color change akin to a pH indicator. Thus, the compositions can contain one or more dyes such as, but not limited to, Lugol's solution, methylene blue, toluidine blue, crystal violet, indigo carmine, Congo red, phenol red and food coloring. In preferred embodiments, the compositions contain methylene blue or indigo carmine.

In some embodiments, the dye is present in an amount which ranges from about 0.0001% to about 0.2% by weight with respect to the weight of the composition, preferably from about 0.0002% to about 0.05% by weight with respect to the weight of the composition, and more preferably from about 0.0005% to about 0.01% by weight with respect to the weight of the composition.

Studies using 1%-3% (RADA)$_4$ (SEQ ID NO: 1) solutions mixed with dextran sulfate solution (0.5 and 1%), formed space occupying gels, which could be tailored for AVMs, internal casts, lifts, etc.

C. Excipients

The formulations may be rehydrated or mixed with excipients suitable for administration onto or into the body. A preferred excipient is sterile water.

Other suitable excipients can be selected based upon the desired assembly-state of the self-assembling peptides precursor materials. For example, when the self-assembling peptides formulations are in the form of a solution, a suitable excipient may contain a concentration of ions below the threshold required to initiate assembly, or may be mixed with ions to initiate assembly prior to or at the time of administration. Suitable buffers are well known by those skilled in the art and include acetate, borate, carbonate, citrate, and phosphate buffers. Formulations may also contain one or more tonicity agents to adjust the isotonic range of the formulation. Suitable tonicity agents are well known in the art and include glycerin, mannitol, sorbitol, sodium chloride, and other electrolytes.

Other additives to the formulation may include pH modifying agents or preservatives to prevent bacterial contamination. Suitable preservatives are known in the art.

D. Dosage Unit Forms and Kits

In some embodiments, formulations of self-assembling peptides are dried or dehydrated to remove fluid, typically using lyophilization.

Kits including self-assembling peptides may also contain diluents, self-assembling peptides with and without dye, needles and/or syringes or other means for administration, and instructions for use. The kit may also include one or more of a pipette, gauze, sponges, cotton, swabs, disinfectant, scissors, a scalpel, a sterile fluid, and disposable gloves.

In some embodiments, the self-assembling peptides formulations in the kit are pre-packaged in a concentrated stock powder or solution, with instructions for diluting to the desired concentration immediately prior to application. When kits include dried self-assembling peptides, they can be packaged with a desiccant. Components of the kit may be packaged individually and be sterile. The kits are generally provided in a container, e.g., a plastic, cardboard, or metal container suitable for commercial sale.

In some embodiments, the kit includes any of the self-assembling peptides, formulations, a suitable means for administration (e.g., an endoscopic injection needle, a syringe), and instructions for use thereof. The kit components may be packaged in primary packaging such as ampules, vials, bottles, pre-filled syringes, pre-filled injection needles, pre-filled catheters and the like.

In some embodiments, the self-assembling peptide formulation is packaged in 1, 2, 5, or 10 mL pre-filled syringes. Suitable endoscopic injection needles may have a diameter of the needle ranging from 12 gauge to 35 gauge, from 15 gauge to 30 gauge, and from 17 gauge to 28 gauge. In some embodiments, suitable endoscopic injection needles have a length ranging from 100 cm to 300 cm, from 120 cm to 260 cm, and from 140 cm to 250 cm. In some embodiments, suitable endoscopic injection needles have an outer diameter ranging from 1.0 mm to 4.0 mm, preferably from 1.5 mm to 3.0 mm, more preferably from 1.8 mm to 2.5 mm.

The self-assembling peptides formulation can be provided as a dry powder in a single dosage unit, typically in combination with sterile diluent to mix at the time of administration. Exemplary volumes for application of solutions of self-assembling peptides to the body include an amount between about 10 µl and about 100 mL, more typically between 0.1 and 1 mL, 1 to 5 mL, or 1 to 10 mL.

A kit containing self-assembling peptides formulated with and without dye allows the clinician to inject the dyed self-assembling, then, if desired, administer non-dyed self-assembling peptides to avoid obscuring the field of view.

III. Methods of Making Self-Assembling Peptide Formulations

Formulations of self-assembling peptides can be prepared using techniques known in the art or purchased, as described above. In some embodiments, the self-assembling peptide formulations are sterilized to remove undesirable contaminants and/or microorganisms. In some embodiments, filtration is used to remove contaminants or microorganisms such as bacteria, cells, protozoa, viruses, fungi, and combinations thereof. In some embodiments, filtration is used to remove aggregated or oligomerized proteins.

Assembly of the self-assembling peptides can be initiated or enhanced before or during upon administration by the addition of an ionic solute or diluent to a solution of self-assembling peptides or by a change in pH. For example, NaCl at a concentration of at least 5 mM can induce the assembly of macroscopic structures within a short period of time, within a few seconds to minutes. Lower concentrations of NaCl may also induce assembly but at a slower rate. More preferably, self-assembly is initiated or enhanced by introducing the SAP into a tissue where it contacts a physiological fluid such as blood, lymph, or tissue secretions.

A wide variety of ions, including anions and cations (whether divalent, monovalent, or trivalent), can be used to induce self-assembly. For example, one can promote a self-assembly by exposure to monovalent cations such as $Li^+$, $Na^+$, $K^+$, $Cs^+$ and $Ca^+$. The concentration of such ions required to induce or enhance self-assembly is typically at least 5 nM to 5 mM. Lower concentrations also facilitate assembly, although at a reduced rate.

Alternatively, some of the self-assembling peptides do not require ions to self-assemble but may self-assemble due to solvent, hydrophobic, and/or side chain interactions, and hydrogen bonding.

The resulting material characteristics, the time required for assembly, and the dimensions of the macroscopic structure that forms are governed by the concentration and amount of solution that is applied, and the concentration of ions used to induce assembly of the structure. The self-assembling peptides can achieve a gel-like or substantially solid form upon self-assembly.

Self-assembly or phase transition is triggered by components found in a subject's body (e.g., ions) or by physiological pH. Self-assembly or phase transition can begin when the compositions are exposed to or brought into contact with a subject's body (e.g., at the mucosa). Self-assembly can occur rapidly upon contact with bodily fluids. The time required for effective assembly and/or phase transition can occur in 60 seconds or less (e.g., in 50, 40, 30, 20, or 10 seconds or less) following contact with a subject's tissue, or to conditions similar to those found within the body. Solutions containing self-assembling peptides can form a self-assembled fluid-impermeable structure upon contact with physiological fluids within times as short as 10 seconds following application. In some circumstances, such as when conditions are sub-optimal or non-physiological, or when the concentration of self-assembling peptide precursors is low, self-assembly or phase transition may take longer to achieve, for example, up to a minute, 5 minutes, 10 minutes, 30 minutes, an hour, or longer.

The compositions can form structures that are substantially rigid (e.g., solid or nearly solid) or that assume a definite shape and volume (e.g., structures that conform to the shape and volume of the location to which a liquid composition was administered, whether in vivo or ex vivo).

IV. Methods of Use

Formulations containing self-assembling peptides and/or self-assembling peptidomimetics, referred to herein jointly as self-assembling peptides unless otherwise specified, can be administered by injection during endoscopic, laparoscopic or otherwise minimally invasive, or open surgical procedures in and/or on the body, including the central nervous, gastrointestinal, genitourinary, integumentary, pulmonary, renal, reproductive, and/or vascular systems, to achieve any of the following:
  a. separation or delineation of tissues and/or organs; lifting, separating, or tunneling beneath or besides tissues, lesions, or medical apparati, such as wires, durable equipment, and closure devices, preferably with sufficient durability (duration) to minimize frequency of injections required to obtain the lift; and preferably with sufficient density for desired separation in the presence of pressure applied during the procedure or natural elastic forces;
  b. visualization or access to tissue or margins during a procedure;
  c. creation of an internal cast or structure that provides support around and/or between tissues or organs to, for instance, enable them to be stabilized, protected, recover, and/or heal, such as after a central nervous system infarction or before, during or after orthopedic or genitourinary procedures; or as bulking agent;
  d. creation of new tissue; and
  e. to smooth wrinkles, scars or other plastic surgery indications.

In the process, the formulation may help to prevent iatrogenic injury; and to concomitantly prevent or stop bleeding, leaking, inflammation, perforation or contamination of tissues, organs and related compartments during any of the above procedures. The formulation is useful prior to excision of adenomas, early-stage cancers or gastrointestinal mucosal lesions as well as for endoscopic management of gastrointestinal bleeding.

a. Separation or Delineation of Tissues and/or Organs

The formulation provides a lift that lasts for at least hours, possesses excellent visualization characteristics, and has hemostatic and sealant activity either prophylactically or in response to bleeding and leaking.

Self-assembling peptides can be administered at any desired target site, such as a region where a minimally invasive procedure is performed. The target site may be a submucosal layer. In some embodiments, the procedure is a gastrointestinal endoscopy performed in the esophagus, stomach, small intestine, cecum, colon, and/or rectum and may be a polypectomy, an EMR or an ESD. In another embodiment, the procedure is performed for the treatment of esophageal varices whereby the formulations, applied topically or injected, are used or as an adjunct to other methods to slow or stop blood flow, visualize and ligate the targeted blood vessels, or treat or lessen the risk of potential perforation. The formulation can be administered through an endoscope, laparoscope, catheter, needle, nebulizer or other device. The formulation can be administered during endoscopic, minimally invasive, or open surgical procedures. Individuals to be treated include subjects with inflammatory tissue, polyps, adenomas, ulcerations, one or more dysplasias, pre-neoplastic and neoplastic formations, vascular malformations, congenital defects, and/or tumors at or near the target site.

The formulations and uses thereof enable less invasive, endoscopic approaches to gastrointestinal procedures (e.g., to remove lesions), improved separation of layers of the gastrointestinal tract for better visualization and treatment, and concomitant management of bleeding and sealing of leaks by topical application or local injection. Typically, layers of the gastrointestinal tract include mucosa (innermost), submucosa, muscularis propria, and adventitia (outermost). Mucosal and submucosal layers can also be subdivided into layers. The examples confirm that the formulations are useful for 1) creating cushions for endoscopic mucosal resections (EMR); 2) establishing tunnels with better margin visualization in endoscopic submucosal dissections (ESD); and 3) providing hemostasis by virtue of forming a contiguous physical-mechanical seal with the wound bed/tissue. The resulting microenvironment is conducive for tissue repair and wound healing. The same benefits are found in removal of tumors and associated tissue repairs.

The formulation may be administered by injection or expression either percutaneously, endoscopically, laparoscopically or otherwise minimally invasively, or during open surgery through a needle or catheter into a tissue to, for instance, create a reservoir of self-assembling peptides. The formulation is injected into the tissue at the site where a lift or tunnel or separation of tissues or structures is desired. The formulations can be applied to any such regions or sites. Exemplary regions or sites include the mucosa, liver, lung, gallbladder, intestines, stomach, colon, rectum, anus, muscle, kidney, artery, vein, brain, spinal cord, peripheral nervous system, eye (including retina), and genitourinary system (including bladder, ureters, uterus, fallopian tubes, and prostate).

The formulations can be applied to provide a cushion or lift (e.g., for an endoscopic resection procedure), to prevent or reduce fluid passage (e.g., to promote hemostasis), and/or to function as a barrier.

The formulations can be used within the gastrointestinal, pulmonary genitourinary, renal, and reproductive systems, which have mucosal surfaces. The formulations can be used for mucosal resection techniques including, but not limited to, EMR, ESD, laparoscopic mucosal resection, uteroscopic mucosal resection, transurethral resection of bladder tumor, and laser mucosectomy. The formulations are particularly useful in endoscopic procedures. Typically, the formulations is administered at a target site (e.g., a submucosal layer) to form a cushion or lift.

The self-assembling peptides are suitable for use in endoscopic resection procedures in the upper and lower gastrointestinal tract, such as the esophagus, stomach, small intestine, colon, sigmoid colon, and rectum, and as a submucosal injectable agent during the removal of polyps, adenomas, early-stage cancers and other pathological lesions by EMR, ESD or polypectomy. The formulations can be injected into the submucosal layer (e.g., by an endoscopic injection needle). When injected, the formulations create a lift in situ by elevating the gastrointestinal mucosa from the submucosal layer, allowing performance of a resection procedure (e.g., EMR, ESD or polypectomy). In some embodiments, the self-assembling peptides self-assemble and/or undergo a phase transition upon contact with a bodily fluid in the submucosal layer. The lift may be fluid, semi-fluid, or gel-like. The lift may withstand the application of pressure during resection (e.g., not dissipate, diffuse or deform).

The formulations can be applied to regions or sites including mucosa and/or surrounding tissues in a subject (e.g., a human). The formulations can be applied to or beneath mucosa intended to be lifted by the formulation. Exemplary regions or sites include submucosa, mucosa, or epithelium. For example, the formulations can be applied to the mucosa or submucosal layer of digestive organs such as the esophagus, stomach, duodenum, bile duct, small intestine, large intestine, colon, and rectum, the mucosa of respiratory organs such as the lung, and the mucosa of genitourinary organs such as the urinary bladder, urethra, vagina, and uterus. Preferably, the formulations are applied to the mucosa of the upper digestive tract (from the esophagus to the stomach or duodenum) and the mucosa of the lower digestive tract (the small intestine, jejunum, ileum lower than the duodenum), and large intestine (colon, rectum).

The formulations can be applied to regions or sites that contain one or more lesions. Examples of relevant lesions are inflammatory tissue, polyps, pseudo-polyps, serrated lesions, adenomas, ulcerations, dysplasias, pre-neoplastic and neoplastic formations, congenital abnormalities, and tumors (including mesenchymal tumors, lymphomas, epithelial tumors, gastrointestinal stromal tumors, among others). Typically, the formulations are administered into the submucosal layer beneath or beside a lesion to provide a lift. The lift is formed such that it is spatially positioned and is of optimal height and/or shape to facilitate resection of a lesion (e.g., polyp or tumor) at or near the target site. The lesion can range in size or volume from about 1 mm to about 20 mm and often more. Larger lesions, such as gastrointestinal stromal tumors, can commonly range in size from about 5 cm to about 8 cm, and can occasionally reach sizes of at least 35 cm.

In some embodiments, the self-assembling peptides are useful for the removal of mucosal lesions, polyps, pseudo-polyps, flat polyps, adenomas, serrated lesions, dysplasias, Barrett's dysplasia, pre-neoplastic formations, neoplastic formations and/or tumors during Surgical procedures.

Polypectomy is a procedure used to remove polyps (an abnormal collection of tissue that extends into the hollow space). A polypectomy can be performed on any area of the body that develops polyps, such as in the uterus, nose, cervix, colon, or stomach. Polypectomy can be performed through open surgery, but more commonly, it is performed minimally invasively.

EMR and ESD are examples of minimally invasive surgery and are the primary surgical options for resection of lesions such as digestive system polyps and malignancies. EMR is an endoscopic technique developed for removal of sessile or flat neoplasms confined to the superficial layers (mucosa and submucosa) of the gastrointestinal tract. EMR is typically used for removal of lesions less than 2 cm in size or piecemeal removal of larger lesions. EMR also plays an important role in the assessment of resected specimens for accurate pathological staging. Various EMR techniques have been described, and four methods involving snare resection are commonly used: inject and cut; inject, lift, and cut; cap-assisted EMR (EMRC); and EMR with ligation (EMRL). The inject and cut technique, also known as submucosal injection polypectomy, has become more widely used because of its simplicity. The diseased mucosa is lifted from the muscular layer by creating a submucosal fluid cushion, and then captured, strangulated, and resected with, for example, an electrosurgical snare.

ESD was developed for wide areas and removing lesions deemed to large to be safely addressed by EMR. Lesions are dissected directly along the submucosal layer using an electrosurgical knife, allowing for en bloc resection of large lesions. ESD is associated with more perforation and bleeding complications than conventional EMR, and requires, therefore, a greater degree of endoscopic skill and experience.

Submucosal injection is essential in most EMR procedures, and it is integral to ESD. Injection lifts the lesion and separates it from the muscular layer, thereby reducing thermal injury and the risk of perforation and bleeding, while making larger en bloc resections technical feasible. Self-assembling peptides can be used for submucosal injection to provide a lift to facilitate the procedure. The elevation of the mucosal surface allows for easier resection of the mucosal lesion even if the lesion is flat and thus not protruding into the lumen. Self-assembling peptides (e.g., in the form of a fluid or gel) can provide lift that remains in the submucosal layer long enough to avoid the need for multiple injections, improve outcomes, reduce adverse events, and minimize damage to tissue specimens in order to allow for accurate pathologic staging. The lift generated by self-assembling peptides can last long enough to allow the endoscopic procedure to be performed with few or no re-injections, lasting for at least 15 minutes, 30 minutes, 1 hour, 2 hours, 3 hours, 4 hours or longer, unlike with other formulations, such as normal saline, which may require repeat injections every couple of minutes.

For example, a solution of self-assembling peptides can be injected in the submucosal layer. Upon contact with a bodily fluid, the self-assembling peptides self-assemble into a gel or gel-like structure that provides mechanical support as a cushion or lift to facilitate resection of a lesion. Additionally, and/or alternatively, the self-assembled structure can prevent or reduce the movement or flow a bodily fluid such as blood. This combination of lift, hemostatic and sealant properties of the self-assembling peptides formulations is advantageous for EMR and ESD.

For Separation of Tissues from Vital Structures or Implants

Self-assembling peptides can be administered for the purpose of separating non-vital tissues from vital structures, including, for example, cranial nerves, biliary ducts, coronary arteries and other critical blood vessels, and sensitive organs or tissues thereby lessening the risk for iatrogenic injury. Disruption of these can be potentially catastrophic to the patient.

Self-assembling peptides can be administered for the purpose of separating tissues and organs from medical implants and devices, such as implantable cardioverter defibrillators and pacemakers (e.g, procedures within or near the pocket), electrodes, stents, breast implants, ocular implants, among others, in order to minimize damaging the device or tissue to which it is implanted.

For Management of Anti-Retropulsion Migration During Lithotripsy

Self-assembling peptides can be administered by ureteroscopy to a site of renal stones to prevent antiretropulsion migration during lithotripsy, as well as to manage bleeding that may occur in surrounding tissue as a result of the procedure. This may be of particular benefit in patients for whom the procedure may be riskier or otherwise contraindicated due to underlying bleeding problems, such as those due to qualitative platelet abnormalities.

For Control of Leakage of Fluid and/or Bleeding

Self-assembling peptide formulations can be administered to prevent rupture of structures. Self-assembling peptides are administered near structures that are at risk of rupturing, resulting in fluid loss, such as from a major artery or the central nervous system, or potential contamination of surrounding tissues, such as with a bowel perforation. In the instances, the formulation allows for better delineation, visualization, and separation of the structures.

Self-assembling peptides may be administered to stop or prevent acute or delayed onset bleeding that is common in procedures requiring a lift, tunneling, tissue delineation, or better visualization, whereby the formulation is applied at, on or adjacent to the site of bleeding. Examples include gastrointestinal, prostate, and central nervous system procedures.

The same method can be used to stop or prevent acute or delayed onset leakage of serum, gastrointestinal fluid, cerebrospinal fluid or other bodily fluids by applying the formulation topically or by injection into the tissue at or near the injection site.

Self-assembling peptides can also be used to provide a seal to a surgical or non-surgical wound alone or in combination with sutures, clips or other devices, at the time of creating lift, tunnels or bulking adjacent to the tissue being treated.

Bleeding is a known complication of EMR and ESD. Intraprocedural ESD bleeding can develop during submucosal injection, incision, or dissection. Submucosal vasculature is abundant in the gastrointestinal tract and, therefore, intraprocedural bleeding occurs commonly. Although about 50% to 70% of bleeding is observed within 2 days of ESD, bleeding can develop as late as 2 weeks after the procedure. Late post-procedural ESD bleeding is a concern because of the challenges associated with providing prompt care after patient discharge.

Self-assembling peptides can be applied to a region or site of interest before, during, and/or after an endoscopic procedure. In some embodiments, the formulations reduce time of hemostasis by at least about 10%, 20%, 30%, 40%, 50%, 60%, 70%, 80%, 90%, or more relative to the time of hemostasis in the absence of the formulation. The formulations may reduce the time required to achieve hemostasis by between 25% and 50%; between 50% and 75%; or between 75% and 100% relative to the time in the absence of the formulation. The time required to achieve hemostasis can be reduced by approximately 2-, 3-, 4-, or 5-fold relative to the time in the absence of the formulation. In some embodiments, administration of the formulations prevents or reduces occurrences of intraprocedural and postprocedural bleeding (e.g., from an endoscopic procedure).

For Management of Complicated Skin Wounds

Self-assembling peptides can be used during debridement of complicated skin wounds, such as burns or chronic wounds. The formulations can provide separation from critical structures and manage bleeding.

They can further be applied between a wound bed and either a skin graft, cellular or tissue based product, or skin equivalent in order to provide separation for a period of time that may be from 1-5 minutes, up to one hour, up to 1 day, up to 7 days, or longer, in order to provide time for the wound bed to adequately heal, become less inflamed, or achieve hemostasis as may be required before direct contact with the applied product is allowed. In such cases, the self-assembling peptides resorb over time.

For Use During Tumor Resection

Self-assembling peptides can be used for the separation and isolation of a tumor or malignant tissue from underlying, surrounding or nearby tissue in order to improve resection and provide clear margins for demarcation. Self-assembling peptides can also help manage bleeding and mitigate hematogenous spread of metastatic tissue. Examples of tumors include, but are not limited to, glioblastoma and acoustic astrocytoma in the brain; breast and prostate cancer; gastrointestinal tumors; melanoma and spindle tumors, including dermatofibrosarcoma, in the skin; hemangioma; hepatocellular carcinoma, adenoma, and focal nodular hyperplasia in the liver; and renal cell carcinoma.

This approach may be particularly beneficial in Mohs Surgery during which a tumor or lesion is removed from a location in which there is a need to obtain or rely on smaller than normal margins, typically because of a nearby vital structure or risk for disfigurement.

For Use During Resection of Arteriovenous Malformations

Self-assembling peptides can be used for the separation, delineation, visualization, isolation and resection of arteriovenous malformations (AVMs) and prevention or treatment of related bleeding. AVMs are abnormal tangles of blood vessels connecting arteries and veins that can disrupt circulation of blood and oxygen. AVMs are prone to weakening and rupture. They may occur throughout the body, but are particularly common in the brain, where a rupture can result in hemorrhage and stroke or brain damage.

b. Visualization or Access to Tissue or Margins During a Procedure

Incorporation of a dye or radiopaque agent ("imaging agent") into the self-assembling peptide formulation enhances one's ability to identify where the formulation has been injected and to delineate the structures separated by the lift, such as the mucosa, the submucosal layer and the external muscular wall, thereby lowering the risk of causing damage. The imaging agent can also help distinguish the cushion cavity from the mucosal basement. The imaging agent can be added to the self-assembling peptides formulation, identifying the area of submucosal injection and distinguishing between the muscle layer and the submucosal layer. This also facilitates identification of the lateral and deep margins of the target lesion before and during the resection process. The imaging agent can also help to evaluate the presence of residual lesions at the end of endoscopic resection and improve recognition of muscularis propria injury, which indicates intraprocedural perforation.

c. For Use as an Internal Cast or to Provide Structural Support

Self-assembling peptides can be used to create an internal cast or structure that provides support around and/or between tissues or organs to, for instance, enable them to be stabilized, protected, recover, and/or heal, such as after a central nervous system infarction or before, during or after orthopedic or genitourinary procedures. In particular, they can be used to stabilize brain parenchyma, including by filling a potential void after hematoma evacuation, as well as to stabilize small, fractured and unstable cartilage or bony structures in lieu of inserting permanent implants.

The self-assembling peptides may also be injected as a bulking agent, where the gel is used in procedures instead of alternatives such as alginate solutions which are cross-lined with calcium ions. Injectable bulking agents are space-filling substances used to increase tissue bulk.

Injectable bulking agents can be used endoscopically in the treatment of both urinary incontinence and vesicoureteral reflux. The advantages in treating urinary incontinence and vesicoureteral reflux with this minimally invasive approach include the simplicity of a quick outpatient procedure and the low morbidity associated with it. The ideal substance for the endoscopic treatment of reflux and incontinence should be injectable, non-antigenic, non-migratory, volume stable, and safe for human use.

When used to treat stress urinary incontinence (SUI), bulking agents are injected periurethrally to increase the tissue bulk and thereby increase resistance to the outflow of urine. Alternatively, the bulking agents are injected transurethrally by advancing a specially designed injection needle through the operative port of a 0-degree cytoscope into the mucosa of the urethra just below the internal urethral sphincter. The bulking agent is then injected at the 4 or 8 o'clock position until the urethral lumen is visibly occluded, and the procedure is repeated on the opposite side.

The use of injectable bulking agents to augment urethral tissue function is now common practice because they facilitate minimally invasive delivery of the bulking agent and provide the advantage of low cost and low patient morbidity. The procedure can be performed in an outpatient setting with the patient under local anesthesia.

d. Creation of New Tissue

Extracellular matrix (ECM) bioscaffolds prepared from decellularized tissues have been used to facilitate constructive and functional tissue remodeling in a variety of clinical applications. The discovery that these ECM materials could be solubilized and subsequently manipulated to form hydrogels expanded their potential in vitro and in vivo utility; i.e. as culture substrates comparable to collagen or Matrigel, and as injectable materials that fill irregularly-shaped defects. The mechanisms by which ECM hydrogels direct cell behavior and influence remodeling outcomes are only partially understood, but likely include structural and biological signals retained from the native source tissue. The ECM consists of the structural and functional molecules secreted by the resident cells of each tissue, hence the 3D organization and biochemical composition of the ECM is distinctive for each tissue type.

Mimicking aspects of the structure and composition of the ECM using self-assembled peptides provides an alternative to these materials as a means of creating new tissue at sites of injection.

e. Smoothing of Wrinkles, Scars or Other Plastic Surgical Indications.

Dermal fillers are gel-like substances that are injected beneath the skin to restore lost volume, smooth lines and soften creases, or enhance facial contours. The fillers are used to smooth out lines around nose and mouth (a.k.a. marionette lines, smile lines, and parentheses), enhance and restore volume to sunken cheeks or temples, diminish vertical lip lines, plump and enhance the lips, smooth out a chin crease, and improve symmetry among facial features.

The self-assembled peptide gels can also be administered to smooth out scar tissue, whether due to injury, surgery or burns.

Effective Amounts

In general, the required amount of self-assembling peptides and formulations thereof varies depending on several factors including, for instance, the specific self-assembling peptides employed, the dimension of the treated area, the desired size of the planned cushion or lift at the target site, and the procedure duration. Other factors that may affect the specific dosage include age, body weight, general health status, sex, time of administration, and severity and course of an underlying disease or condition. The administered dosage, volume or concentration may vary depending upon the form of the self-assembling peptides (for example, in a peptide solution, hydrogel) and the route of administration. In certain embodiments, the self-assembling peptide formulation is administered in a single dose. In other embodiments, the self-assembling peptide formulation is administered in two or more doses.

An effective amount, whether in reference to self-assembling peptides and/or other agents present in the formulations, means the amount necessary to elicit a desired response or effect. For example, in some embodiments, the self-assembling peptides formulation is administered in an amount to form a desired cushion or lift at a target site (e.g., in submucosal layer beneath a lesion).

In another example, an effective amount can be an amount of a self-assembling peptides formulation that accelerates hemostasis, such as an amount sufficient to decrease blood loss between the onset and cessation of bleeding by at least 25% relative to comparable blood loss in the absence of the formulation. An effective amount of a formulation for accelerating hemostasis may also be an amount sufficient to decrease the time to cessation of visible bleeding by at least 25% relative to comparable time in the absence of the formulation.

The effective amount may vary depending on the desired size of the resulting cushion or lift and/or the degree of bleeding. The amount may vary, for example, from a few microliters to several milliliters or more, e.g., tens or hundreds of milliliters. In some embodiments, the effective amount may include volumes of from about 0.1 milliliters (mL) to about 100 mL of a self-assembling peptides solution. In certain embodiments, the effective amount may be about 0.5 mL, 1.0 mL, 1.5 mL, 2.0 mL, or 3.0 mL of a self-assembling peptides solution. In certain embodiments, the effective amount may be approximately 0.1 mL to about 5 mL per 1 $cm^2$ of target area.

Useful concentrations of self-assembling peptides in the formulations can range from between approximately 0.1-10% (e.g., 0.1-2%; 0.1-3%; 0.1-4%; 0.1-5%; 0.5-5%; 1-3%; 1-4%; 1-6%; 1-8%, and 1-10%) expressed in weight/volume or volume/volume. Any subrange, or any specific value within any of the aforesaid ranges, can be used. The effective amounts may include self-assembling peptides concentrations in solution of about 1% w/v. In other embodiments, the effective amounts may include self-assembling peptides concentrations of about 1.5%, 2%, 2.5%, 3%, 3.5%, or 4% w/v.

Methods of Administration

The self-assembling peptides and formulations can be administered via any means which is effective to deliver an effective amount to a site in need thereof. In some embodiments, the formulations are delivered directly to the target site/surface using mechanical delivery means, e.g., dropping and/or spraying.

Delivery devices that may be used include a syringe, pipette, tube, endoscope, laparoscope, catheter, syringe catheter, or other needle-based device. In preferred embodiments, the formulations are administered to the target site through an endoscope, laparoscope, or catheter. The use of a catheter may provide for selective administration of the formulation to provide for a more accurate delivery to the target site. Administration of the formulation may allow for enhanced and more targeted delivery of the self-assembling peptides solution, such that formation of a cushion or lift is successful and positioned in the desired location in an accurate manner.

In some embodiments, the self-assembling peptides formulation is administered to a target site through injection by means of an endoscopic injection needle. For example, in some embodiments, an effective amount of a self-assembling peptides formulation is administered by means of an endoscopic injection needle inserted through the working channel of the endoscope. The endoscopic injection needle can be positioned to facilitate deposition of the formulation immediately under the superficial mucosal layer or a lesion, or to deposit the formulation (e.g., a liquid) into the submucosal layer.

All references cited herein are incorporated by reference in their entirety. The present description will be further understood by reference to the following non-limiting examples.

EXAMPLES

Example 1: Self-Assembling Peptides Form Submucosal Cushions and Promote Hemostasis in Endoscopic Resection Procedures in a Porcine Model Materials and Methods Solutions of $(RADA)_4$ (RADARADARADARADA; SEQ ID NO: 1) in water were prepared. Concentrations of $(RADA)_4$ (SEQ ID NO: 1) were between from 1% and 3% w/v. Methylene blue or indigo carmine dye (0.1 to 0.4%) was added to the solution in some experiments, and excluded from the solution in other experiments.

Pigs were randomly assigned to control or experimental groups. Animals were anesthetized. Multiple (>20) endoscopic procedures (EMD and ESD) were performed in different areas of the stomach of pigs, including the pylorus, and the esophagus, including the sphincter. In some experiments, polyps had previously been created by applying bands to the mucosa.

The $(RADA)_4$ (SEQ ID NO: 1) solutions (experimental animals) or saline or ELEVIEW™ (control animals) were administered into the submucosal space through 2.2 mm channel diameter, 230 cm long catheters that have either 25 gauge needle tips or spray tips on the end to form a cushion. In some experiments, catheters having different diameters were used as well as multiple internal channels. The products were delivered from a prefilled syringe or mixed from a kit prior to delivery.

Results

Experiments were performed to investigate the use of SAP in gastrointestinal tract endoscopic procedures. The cushion forming ability of the different $(RADA)_4$ (SEQ ID NO: 1) formulations was evaluated using several procedures in pigs. The porcine model was used because it is a widely accepted model of the human gastrointestinal mucosa.

Multiple procedures were performed, including endoscopic mucosal resections, endoscopic submucosal dissections and hemostasis of post-polypectomy beds. $(RADA)_4$ (SEQ ID NO: 1) was easily delivered through a 25G endoscopic injection needle and provided a durable submucosal lift in the gastric antrum that lasted beyond 2 hours. When delivered with the visualizing agent prior to tissue dissection, $(RADA)_4$ (SEQ ID NO: 1) allowed for easy visualization with both snare and electrosurgical knives, and no visible bleeding was observed following polyp removal. It was also shown to provide hemostasis in actively bleeding lesions when applied with or without the visualizing agent, either topically to a bleeding site or when injected into the nearby mucosa. Furthermore, $(RADA)_4$ (SEQ ID NO: 1) was found to be useful in conjunction with clips as a potential sealant when applied following application of clips to a post-polypectomy site for the purpose of mitigating leaks and potentially enabling healing.

Submucosal injection of $(RADA)_4$ (SEQ ID NO: 1) solutions created cushions. With good visibility, mucosal tissue above the cushion was easily removed with snares. In other cases, the tissue was dissected while a submucosal tunnel was created and elongated with simultaneously application of the formulation; tissue representing the roof of the tunnel was removed. In other cases, a long cushion was created, and a submucosal tunnel was dissected subsequently. Tissue representing the roof of the tunnel was removed. In some procedures, minimal to no bleeding in most lesions was observed, indicating that the self-assembling peptide solution was prophylactically hemostatic. In a few lesions that bled, or in cases where bleeding was created intentionally, direct application of the $(RADA)_4$ (SEQ ID NO: 1) solution, either topically or by injection, into the mucosa near the bleeding site stopped bleeding promptly, typically within seconds. During the procedures, the $(RADA)_4$ (SEQ ID NO: 1) solutions were easily used as an adjunct to clips to achieve hemostasis and prevent leaks in large wounds.

The $(RADA)_4$ (SEQ ID NO: 1) solutions produced cushions that were of significant height that provided adequate lift/cushion. After formation of the mucosal lift/cushion, polyps were easily removed. It was easier to control the degree of lift provided by the $(RADA)_4$ (SEQ ID NO: 1) solution versus saline, which is traditionally used. $(RADA)_4$ (SEQ ID NO: 1) cushions remained intact where locally injected without evidence of dissipating or traveling away. The $(RADA)_4$ (SEQ ID NO: 1) cushions were highly durable (the duration of submucosal elevation could be measured in hours), while also possessing prophylactic hemostatic and sealant properties. The durability of the (RADA)$_4$ (SEQ ID NO: 1) cushions was pronounced, lasting longer than ELEVIEW™ and saline controls. The (RADA)$_4$ (SEQ ID NO: 1) cushions permitted safe and efficient performance of EMR as a single injection without need for subsequent injections, even hours later.

The (RADA)$_4$ (SEQ ID NO: 1) cushions could be easily dissected through and tissue could be resected/dissected using a range of devices, including hot and cold snares and knives (including hot/energized or cold) knives.

Excellent ability to tunnel through the (RADA)$_4$ (SEQ ID NO: 1) cushions was observed, even for long distances, up to centimeters in length. Easy injection of the (RADA)$_4$ (SEQ ID NO: 1) compositions into the lumen and dissection into tunnels through the layers as desired was performed with excellent visibility and over prolonged periods of time. When (RADA)$_4$ (SEQ ID NO: 1) cushions were created, the clinician/endoscopist could easily find the tunnel opening whenever the equipment was removed and reinserted. This was observed over extended periods of time, typically more than an hour.

The (RADA)$_4$ (SEQ ID NO: 1) solutions with dye or without dye were applied as desired. This was determined by whether or not contrast was preferred in the given situation. In some topical application situations, contrast can obscure the visual field. This was not the case in any procedures requiring injection.

Collectively, these results show that self-assembling peptides can be used to create cushions or lifts during endoscopic procedures. Self-assembling peptides cushions/lifts in the submucosal layer facilitate easy removal of polyps and other lesions. The self-assembling peptides cushions/lifts show high duration, obviating the need for multiple injections. The cushions/lifts are expected to be resorbed over time. The self-assembling peptides cushions limit or prevent bleeding (i.e., prophylactically), but the self-assembling peptides formulations can also be applied topically or by injection to stop bleeding during and/or after the procedure.

Example 2: Tumor Resections Using SAPS

The formulations were tested to confirm their usefulness for the separation and the isolation of tumor and tumor tissue from the underlying and surrounding tissue that contains the tumor. This creates a resection pathway and a clear margin for demarcation during resection. In addition, it stops bleeding and flow of any tissue out of the tumor to contain metastases.

Materials and Methods

Prostrate tumors were subcutaneously implanted in nude mice.

Formulations of (EARA)$_4$ (SEQ ID NO: 89), (RADA)$_4$ (SEQ ID NO: 1), and other sequences, were injected to lift and separate the tumor from the surrounding tissue during resection.

Results

The SAP formulations were effective to hold loose tumors together so that when they were resected, nothing was left behind. This also helped to insure good margins were obtained. In addition to bleeding control, there is also metastatic control. The margins are clearly visible as well.

Example 3: Rheology and Injection Force Assessment of Self-Assembling Peptides Formulations Materials and Methods AC5-G Solution Preparation (RADA)$_4$ peptide (SEQ ID NO: 1) from Arch Biosurgery (also referred to as AC5) was used. 1.5%, 2.0% and 3% solutions of (RADA)$_4$ (SEQ ID NO: 1) were prepared using an aqueous solution of 0.004% Methylene Blue (MB) NF grade in SpeedMixer™ cups. The cups were then transferred to the SpeedMixer™ and run at 3,000 rpm for 5 minutes. The solutions were examined for uniformity and air bubbles. The solutions were then quickly transferred into BD syringes and filtered through a 0.2u PES syringe filter. The filtered solutions were filled in Schott 5 cc TopPac COC Syringes.

Injection Force Measurements

A calibrated Mark-10 force gauge and motorized stand (travel speed was 1.5"/min) were used to measure the injection force of solutions from 5 cc syringe connected to 240 cm×23G BSC Interject catheter needle.

Rheology Assessment

Peptide solution: A TA instruments DHR-2 rheometer with a parallel plate configuration was set up. Each test solution was vortexed for 5 minutes and then 130 microliters of solution was placed on the Peltier plate previously equilibrated 25° C. The 20 mm steel parallel plate geometry was lowered to a gap of 325 micrometer contacting the peptide solution on the Peltier plate. Time sweep data was collected under strain controlled conditions: Frequency 1 Hz, Strain 0.1%, Time 10 minutes, delay time 10 seconds.

Peptide solution mixed with human sera: A TA instruments DHR-2 rheometer with a parallel plate configuration was set up. Each test solution was vortexed for 5 minutes. First, 65 microliters of human sera was added to the center of the Peltier plate (precooled to 5° C.) and then 65 microliters of peptide solution was added. Both solution were mixed together briefly with a pipette tip. The 20 mm steel parallel plate geometry was lowered to a gap of 325 micrometer contacting the peptide solution on the Peltier plate. The test was started within one minute of mixing the peptide with human sera. Time sweep data was collected under torque controlled conditions: Frequency 1 Hz, Torque: 20 μN·m, Temperature: 37° C. (heating from 5° C. as fast as possible during the experiment), Time 30 minutes, delay time 10 seconds.

Results

Table 2 shows the results from the injection force experiments.

TABLE 2

Injection force measurements.

| Solution | Injection Force (N) |
|---|---|
| 1.5% AC5/0.004% MB | 13-15 |
| 2.0% AC5/0.004% MB | 23-24 |
| 3.0% AC5/0.004% MB | 58-61 |

The injection force results show that as concentration of the self-assembling peptide increases, it generates viscosity/ rheological property such that it will require a larger force to inject the solution through a needle catheter into tissue. It is believed that if water were to be injected in this experiment instead, the value for injection force would be less than 10 N (data not shown). Tables 3 and 4 show the results from the rheology assessments.

TABLE 3

Rheology measurements for peptide solutions.

| Solution | Start/End | G' [Pa] | G'' [Pa] |
| --- | --- | --- | --- |
| 1.5% AC5/0.004% MB | start | 3.133 | 2.851 |
|  | end | 3.751 | 3.171 |
| 2.0% AC5/0.004% MB | start | 2.963 | 3.356 |
|  | end | 4.083 | 4.018 |
| 3.0% AC5/0.004% MB | start | 8.216 | 8.064 |
|  | end | 34.25 | 17.17 |

TABLE 4

Rheology measurements for peptide solutions mixed with human sera.

| Solution | Start/End | G' [Pa] | G'' [Pa] |
| --- | --- | --- | --- |
| 1.5% AC5/0.004% MB | start | 944.3 | 273 |
|  | end | 2504 | 298.2 |
| 2.0% AC5/0.004% MB | start | 1868 | 485.7 |
|  | end | 4557 | 447.6 |
| 3.0% AC5/0.004% MB | start | 2310 | 674.5 |
|  | end | 6580 | 665.5 |

The rheological results show that the G' (storage modulus, which is an indicator of the elastic behavior/mechanical property) value increases with concentration. When G'>G", this indicates that the solution is more like a gel than a viscous solution. The G' values were lower in the absence of sera (Table 3) as compared to the presence of sera (Table 4). The experiments in which the peptide solutions were mixed with sera show that i) AC5-G self assembles and the mechanical strength of the resulting gel is dependent on the concentration of the peptide, and ii) the addition of methylene blue did not affect the self-assembling property of the solution (similar trends were observed for the AC5 peptide solutions with or without methylene blue).

Overall, it is contemplated that the rheology and injection force experiments described above can inform the selection of the concentration for a self-assembling peptide formulation. For example, in some embodiments a formulation that requires a lower injection force but reasonable G' value post mixing with serum is useful as a lift solution and hemostat.

Unless defined otherwise, all technical and scientific terms used herein have the same meanings as commonly understood by one of skill in the art to which the invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method comprising administering in vivo to a site in or on a subject in need thereof an effective amount of a biocompatible, injectable formulation comprising one or more self-assembling peptides which forms a lift or bulking agent having a duration of at least 30 minutes and an injection force of 13 N or greater,
wherein the self-assembling peptides comprise RADARADARADARADA (SEQ ID NO: 1) and/or EARAEARAEARAEARA (SEQ ID NO: 89),
in a concentration between about 2% up to about 6% w/v, to
separate or delineate tissues and/or organs or tumors;
lift, separate, or tunnel beneath or besides tissues, lesions, or a medical apparatus selected from wires, durable equipment, and closure devices;
form a cushion or lift at a target site comprising a lesion, visualize or access tissue or margins during a procedure;
create an internal cast or structure that provides support around and/or between tissues or organs, enabling them to be stabilized, protected, recover, and/or heal,
provide a bulking agent;
provide a matrix for creation of new tissue; and/or
smooth wrinkles or scars,
wherein the formulation persists for at least one hour.

2. The method of claim 1, wherein the concentration of self-assembling peptides in the formulation is about 3% w/v, and is injectable from a needle between tissue layers with an injection force of at least 58 N.

3. The method of claim 1, wherein the formulation comprises one or more therapeutic agents, prophylactic agents, or diagnostic agents.

4. The method of claim 1, comprising a dye or radiopaque agent.

5. The method of claim 1 for use in separation or delineation of tissues and/or organs.

6. The method of claim 1 for use in lifting, separating, or tunneling beneath or besides tissues, lesions, or a medical apparatus selected from wires, durable equipment, and closure devices.

7. The method of claim 6 for separation and visualization of biliary and pancreatic vessels during surgical procedures.

8. The method of claim 1 for use in visualization or access to tissue or margins during a procedure.

9. The method of claim 1 for use in creation of an internal cast or structure that provides support around and/or between tissues or organs to enable them to be stabilized, protected, recover, and/or heal.

10. The method of claim 9 for making an internal cast.

11. The method of claim 8 for treatment of an arteriovenous malformation or for management of antiretropulsion migration during lithotripsy.

12. The method of claim 1 for use in creation of new tissue.

13. The method of claim 1 for use in smoothing wrinkles or scars.

14. The method of claim 1 for separating a tissue or tumor during resection or repair, comprising injecting the formulation into the tissue adjacent to the tissue or tumor to be repaired, in an amount effective for the formulation to solidify to form a lift, tunnel or barrier around the tissue or tumor which persists throughout the resection or repair.

15. The method of claim 14, wherein the tissue is a polyp in a mucosal surface.

16. The method of claim 14, wherein the cushion or lift is of a height and/or shape to facilitate resection of the tissue or tumor.

17. The method of claim 1, wherein the method is performed percutaneously, endoscopically, laparoscopically or by injection through a needle or catheter.

18. The method of claim 1, wherein the formulation is administered in the central nervous, gastrointestinal, genitourinary, integumentary, pulmonary, renal, reproductive, and/or vascular systems.

19. The method of claim 1, wherein the subject is human.

20. The method of claim 1, wherein the concentration of self-assembling peptides in the formulation is between about 3% w/v and about 4% w/v, inclusive.

21. The method of claim 6 for use in lifting, separating, or tunneling beneath or besides tissues, lesions, or a medical apparatus selected from wires, durable equipment, and closure devices, with durability effective to minimize frequency of injections required to obtain the lift; and with a density effective to produce separation in the presence of pressure applied during a procedure or natural elastic forces.

22. The method of claim 1 wherein the concentration of self-assembling peptides in the formulation is about 2.5% w/v.

23. The method of claim 1 wherein the formulation has a duration of at least two weeks.

24. The method of claim 1 wherein the formulation produces greater lift than saline.

* * * * *